US012570725B2

(12) United States Patent
Permar et al.

(10) Patent No.: US 12,570,725 B2
(45) Date of Patent: Mar. 10, 2026

(54) ZIKA ANTIBODIES AND THEIR USE

(71) Applicant: Duke University, Durham, NC (US)

(72) Inventors: Sallie Permar, Durham, NC (US);
Mattia Bonsignori, Durham, NC (US);
Tulika Singh, Durham, NC (US);
Kwan-Ki Hwang, Durham, NC (US)

(73) Assignee: Duke University, Durham, NC (US)

( * ) Notice: Subject to any disclaimer, the term of this patent is extended or adjusted under 35 U.S.C. 154(b) by 1031 days.

(21) Appl. No.: 17/642,674

(22) PCT Filed: Sep. 11, 2020

(86) PCT No.: PCT/US2020/050549
§ 371 (c)(1),
(2) Date: Mar. 11, 2022

(87) PCT Pub. No.: WO2021/050989
PCT Pub. Date: Mar. 18, 2021

(65) Prior Publication Data
US 2022/0315646 A1      Oct. 6, 2022

Related U.S. Application Data

(60) Provisional application No. 62/900,201, filed on Sep. 13, 2019.

(51) Int. Cl.
*C07K 16/10* (2006.01)
*A61P 31/14* (2006.01)
A61K 39/00 (2006.01)

(52) U.S. Cl.
CPC .............. *C07K 16/10* (2013.01); *A61P 31/14* (2018.01); *A61K 2039/505* (2013.01); *A61K 2039/55* (2013.01); *C07K 2317/21* (2013.01); *C07K 2317/33* (2013.01); *C07K 2317/52* (2013.01); *C07K 2317/71* (2013.01)

(58) Field of Classification Search
CPC .......................... C07K 16/10; A61K 2039/505
See application file for complete search history.

(56) References Cited

U.S. PATENT DOCUMENTS

| | | | |
|---|---|---|---|
| 8,278,036 B2 | 10/2012 | Kariko et al. | |
| 8,691,966 B2 | 4/2014 | Kariko et al. | |
| 8,748,089 B2 | 6/2014 | Kariko et al. | |
| 8,835,108 B2 | 9/2014 | Kariko et al. | |
| 9,012,219 B2 | 4/2015 | Kariko et al. | |
| 9,371,511 B2 | 6/2016 | Kariko et al. | |
| 9,750,824 B2 | 9/2017 | Kariko et al. | |
| 10,006,007 B2 | 6/2018 | Kariko et al. | |
| 10,064,935 B2 | 9/2018 | Ciaramella et al. | |
| 10,232,055 B2 | 3/2019 | Kariko et al. | |
| 11,028,370 B2 | 6/2021 | Kariko et al. | |
| 11,060,107 B2 | 7/2021 | Weissman et al. | |
| 11,117,954 B2 | 9/2021 | Corti | |
| 2003/0091995 A1 | 5/2003 | Buechler et al. | |
| 2012/0251544 A1 | 10/2012 | Jackson et al. | |
| 2016/0032316 A1 | 2/2016 | Weissman et al. | |
| 2018/0344838 A1 | 12/2018 | Ciaramella et al. | |
| 2019/0256582 A1* | 8/2019 | Corti ...................... A61P 31/20 |

FOREIGN PATENT DOCUMENTS

| | | |
|---|---|---|
| WO | 2004/076677 | 9/2004 |
| WO | 2010/046775 | 4/2010 |
| WO | 2010/053987 | 5/2010 |
| WO | 2011/126577 | 10/2011 |
| WO | 2016/176330 | 11/2016 |
| WO | 2017/182524 | 10/2017 |
| WO | 2018/081638 | 5/2018 |

OTHER PUBLICATIONS

Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding. PNAS Jan. 24, 2017 114(4) E486-E495;firstpublished Jan. 5, 2017. (Year: 2017).*
Kussie et al. A single engineered amino acid substitution changes antibody fine specificity.J Immunol. Jan. 1, 1994;152(1):146-52. (Year: 1994).*
Wu et al. Humanization of a murine monoclonal antibody by simultaneous optimization of framework and CDR residues. J Mol Biol. Nov. 19, 1999;294(1):151-62. (Year: 1999).*
Oyen et al. Nucl Med Commun 1996, 17: 616-20.
Petersen LR, Jamieson DJ, Powers AM, Honein MA. Zika Virus. N Engl J Med. Apr. 21, 2016;374(16):1552-63.
Randall TD et al. PNAS, 1992, 89: 962-966.
Rasmussen et al., 2016 N Engl J Med 2016; 374:1981-1987.
Reynolds et al., 2017 MMWR Morb Mortal Wkly Rep 2017; 66:366-373.

(Continued)

*Primary Examiner* — Aurora M Fontainhas
*Assistant Examiner* — Jennifer A Benavides
(74) *Attorney, Agent, or Firm* — Baker Donelson

(57) ABSTRACT

The invention is directed to antibodies, and antigen-binding fragments thereof, that potently neutralize infection of ZIKV. The invention also relates to antigenic sites to which the antibodies and antigen-binding fragments bind, as well as to nucleic acids that encode the antibodies of the invention, and immortalized B cells that produce such antibodies and antibody fragments. In addition, the invention relates to the use of the antibodies and antibody fragments of the invention in screening methods as well as in the diagnosis, prophylaxis and treatment of ZIKV infection.

15 Claims, 31 Drawing Sheets

Specification includes a Sequence Listing.

(56) References Cited

OTHER PUBLICATIONS

Richner et al Cell Jul. 13, 2017; 170(2): 273-283.e12.

Rothman, A.L, Dengue: defining protective versus pathologic immunity. J Clin Invest. 113, 946-951 (2004).

Rubin et al. Zika Virus and Microcephaly. N Engl J Med (2016), doi: 10.1056/NEJMe 1601862).

Sapparapu et al., Nature Dec. 15, 2016; 540 (7633): 443-447.

Sarno M, Sacramento GA, Khouri R, do Rosário MS, Costa F, et al. (2016) Zika Virus Infection and Stillbirths: A Case of Hydrops Fetalis, Hydranencephaly and Fetal Demise. PLOS Neglected Tropical Diseases 10(2): e0004517. https://doi.org/10.1371/journal.pntd.0004517.

Screaton, G. et al., New insights into the immunopathology and control of dengue virus infection. Nat Rev Immunol. 15, 745-759 (2015).

Singh T et al. PLoS Negl Trop Dis Aug. 26, 2019; 13(8): e0007648.

Sirohi et al., The 3.8 Å resolution cryo-EM structure of Zika virus. Science aaf5316 (2016).

Song et al., Zika virus NS1 structure reveals diversity of electrostatic surfaces among flaviviruses, 1-6 (2016).

Suy A, Sulleiro E, Rodó C, Vázquez É, Bocanegra C, Molina I, Esperalba J, Sánchez-Seco MP, Boix H, Pumarola T, Carreras E. Prolonged Zika Virus Viremia during Pregnancy. N Engl J Med. Dec. 29, 2016;375(26):2611-2613.

Tang et al., Cell Stem Cell, (2016) 18, 587-590.

Written opinion of the International Searching Authority for PCT/US2020/050549 mailed Feb. 10, 2021.

Bonsignori et al. J Virol Oct. 2011; 85(19): 9998-10009.

Bonsignori et al., Immunity Dec. 18, 2018; 49(6): 1162-1174 e8.

Brasil et al., N Engl J Med 2016; 375:2321-2334.

Broutet N, Krauer F, Riesen M, Khalakdina A, Almiron M, Aldighieri S, Espinal M, Low N, Dye C. Zika Virus as a Cause of Neurologic Disorders. N Engl J Med. Apr. 21, 2016;374(16):1506-9.

Calvet, et al., Detection and sequencing of Zika virus from amniotic fluid of fetuses with microcephaly in Brazil: a case study. Lancet Infect Dis (2016), doi: 10.1016/s I 473-3099(16)00095-5.

Cao-Lormeau and Musso, Emerging arboviruses in the Pacific. Lancet. 384, 1571-1572 (2014).

Cao-Lormeau et al., Guillain-Barre Syndrome outbreak associated with Zika virus infection in French Polynesia: a case-control study. Lancet. 0 (2016), doi: I 0.1016/S0140-6736(16)00562-6.

Collins et al., Emerg Infect Dis May 2017; 23(5): 773-781.

Cugola et al., 2016, Nature, 534, 267-271 (2016).

D. Musso et al., Potential sexual transmission of Zika virus Emerg Infect Dis. 21, 359-361 (2015).

D.L. Heymann et al., Zika virus and microcephaly: why is this situation a PHEIC? Lancet. 387, 719-721 (2016).

Dai et al., Structures of the Zika Virus Envelope Protein and Its Complex with a Flavivirus Broadly Protective Antibody. Cell Host Microbe (2016).

Dang J, Tiwari SK, Lichinchi G, Qin Y, Patil VS, Eroshkin AM, Rana TM. Zika Virus Depletes Neural Progenitors in Human Cerebral Organoids through Activation of the Innate Immune Receptor TLR3. Cell Stem Cell. Aug. 4, 2016;19(2):258-265.

Davis, AC et al. Eur. J. Immunol. 1988: 18, 1001-1008.

Dejnirattisai, W. et al. Dengue virus sero-cross-reactivity drives antibody-dependent enhancement of infection with zika virus. Nat Immunol. Jun. 2016, 23. PMID 27339099.

Driggers et al., N Engl J Med Jun. 2, 2016; 374(22):2142-51.

Duffy et al., Zika virus outbreak on Yap Island, Federated States of Micronesia. N Engl J Med. 360, 2536-2543 (2009).

F.N. Macnamara, Zika virus: a report on three cases of human infection during an epidemic of jaundice in Nigeria. Trans. R. Soc. Trop. Med. Hyg. 48, 139-145 (1954).

Fauci and Morens, N Engl J Med Feb. 18, 2016;374(7):601-4.

G.W. A. Dick, S.F. Kitchen, A.J. Haddow, Zika virus. I. Isolations and serological specificity. Trans. R. Soc. Trop. Med. Hyg. 46, 509-520 (1952).

Gao et al. Cell Jul. 31, 2014; 158(3).

Gennaro (2000) Remington: The Science and Practice of Pharmacy, 20th edition, ISBN: 0683306472.

Gilmour et al. Transfusion Medicine, 2008, 18: 167-174.

Halstead, S.B. Dengue Antibody-Dependent Enhancement: Knowns and Unknowns. Micerobiol Spectr. 2, 249-271 (2014).

Halstead, S.B et al., Dengue hemorrhagic fever in infants: research opportunities ignored. Emerging Infect Dis. 8, 1474-1479 (2003).

Halstead, S.B., Neutralization and antibody-dependence enhancement of dengue viruses. Adv Virus Res. 60, 421-467 (2003).

Hamel R, Liégeois F, Wichit S, Pompon J, Diop F, Talignani L, Thomas F, Desprès P, Yssel H, Missé D. Zika virus: epidemiology, clinical features and host-virus interactions. Microbes Infect. Jul.-Aug. 2016;18(7-8):441-9. doi: 10.1016/j.micinf.2016.03.009. Epub Mar. 22, 2016.

Hills et al., MMWR Morb Mortal Wkly Rep 2016;65:215-216.

Hiramoto et al. Sci. Adv. 2018; 4: eaau1199.

Holliger and Hudson, 2005, Nature Biotechnology 9: 1126-1136.

Hughey CT et al. J. Immunol. 1998, 161, 4091-4097.

International Search Report for PCT/US2020/050549 mailed Feb. 10, 2021.

Kohler, G and Milstein, C. Continuous cultures of fused cells secreting antibody of predefined specificity, Nature vol. 256, 1975.

L. R. Baden, L. R. Petersen, D. J. Jamieson, A. M. Powers, M.A. Honein, Zika Virus. N. Engl. J. Med. 374, 1552-1563 (2016).

Lazear et al., 2016 Cell Host Microbe May 11, 2016;19(5):720-30.

Levin MJ, (2019) Varicellazoster immunoglobulin (VARIZIG) administration up to 10 days after varicella exposure in pregnant women, immunocompromised participants, and infants: Varicella outcomes and safety results from a large, open-label expanded-access program. PLoSONE 14(7): e0217749.

Li C, Xu D, Ye Q, Hong S, Jiang Y, Liu X, Zhang N, Shi L, Qin CF, Xu Z. Zika Virus Disrupts Neural Progenitor Development and Leads to Microcephaly in Mice. Cell Stem Cell. Jul. 7, 2016;19(1):120-6.

Liao et al. J Virol Methods Jun. 2009; 158(1-2): 171-9.

Long, Feng, et al. "Structural basis of a potent human monoclonal antibody against Zika virus targeting a quaternary epitope." Proceedings of the National Academy of Sciences 116.5 (2019): 1591-1596.

Luo et al. Blood Feb. 12, 2009: 113(7): 1422-31.

Meaney-Delman et al., 2016 MMWR Morb Mortal Wkly Rep 2016; 65: 211-214.

Mlakar et al., N Engl J Med, (2016), 374, 951-8.

Moh ES et al J Am Soc Mass Spectrom. Jul. 2016; 27(7): 1143-55.

Muller and Young, The Flavivirus NS1 protein: molecular and structural biology, immunology, role in pathogenesis and application as a diagnostic biomarker. Antiviral Res. 98, 192-208 (2013).

Musso et al., Rapid spread of emerging Zika virus in the Pacific area. Clin. Microbiol. Infect. 20, 0595-6(2014).

Musso, D. et al., Zika virus: following the path of dengue and chikungunya? The Lancet. 386, 243-244 (2015).

Nguyen, T.H. et al., Dengue hemorrhagic fever in infants: a study of clinical and cytokine profiles. J Infect Dis. 189, 221-232 (2004).

Norderhaug IN et al. Crit Rev Immunol 1999, 19: 481-508.

Collins, Cathy, Florence WL Tsui, and Marc J. Shulman. "Differential activation of human and guinea pig complement by pentameric and hexameric IgM." European journal of immunology 32.6 (2002): 1802-1810.

Kozbor, Danuta, and John C. Roder. "The production of monoclonal antibodies from human lymphocytes." Immunology Today 4.3 (1983): 72-79.

* cited by examiner

ARB73 (Early Convalescent) Gating Strategy

FSC Singlets

SSC Singlets

Figure 2A

* Human B cell line was derived.

* Human B cell line was derived.

ARB73 (Early Convalescent)
120-1-D7 Monoclonal Antibody ZIKV Binding

| | IgM | IgG |
|---|---|---|
| FRNT50 in ng/ml | 24.7 ng/ml | 149.5 ng/ml |
| FRNT50 in pM | 25.5 pM | 996.7 pM |

Figure 10

ATTACHMENT No. 1

Genetic sequences and identifying information for each of the mAbs generated so far has been provided below.

1. HEAVY CHAIN SEQUENCES: CDRH1, CDRH2 and CDRH3 are underlined and in bold and are always in this order.
2. LIGHT CHAIN SEQUENCES (both kappa and lambda): CDRL1, CDRL2 and CDRL3 are underlined and in bold and are always in this order.

Raw Sequences in fasta format

Heavy Chain Sequences

>H621097
GAGGTGCAGCTGGTGGAGTCTGGGGGGGGCCTGGTCAAGCCTGGGGGGTCCCTGCGACTCTCCT
GTGTAGCCTCTGGATTCACCTTCAATATTTATAATATGAACTGGGTCCGCCAGGCTCCTGGGAG
GGGGCTGGAATGGGTCTCATCCATTAGTCTTAGTAGTAGTTACATAGACTACGCAGACTCAGTG
GAGGGCCGGTTCACCATCTCCAGAGACAACGCCAAGAACTCACTGTCTCTGCAAATGAACAGTT
TGAAAGCCGAAGACACAGCTGTCTACTACTGT**GCGAGAGGTCGCCGGGGGGAGTGGCTGGTGCT
ACATGATGCTTTTGATCTC**TGGGGCCAGGGGACATTGGTCACCGTCTCTTCAG

>H621157
GAGGTGCAGCTGGTGGAGTCTGGGGGGGGCTTGGTACAGCCTGGGGGGTCCCTGAGACTCTCCT
GTGCAGCCTCTGGATTCACCTTTAGCAGCTGTGCCATGACCTGGGTCCGCCAGGCTCCAGGGAA
GGGGCTGGAGTGGGTCTCAGTCATTAGTGGTAGTGGTGGTAGTACATACTACGCAGACTCCGTG
AAGGGCCGGTTCTCCATCTCCAGAGACAATTCCAAGAACACGCTGTATCTGCAAATGAACAGCC
TGAGAGCCGAGGACACGGCCGTATATTACTGT**GCGAAAAGCTGGGGGGATTACTATGATAGTAG
TGGTTACCCCGTTTACTACTACTACTAC**TACATGGACGTCTGGGGCAAAGGGACCACGGTCACC
GTCTCCTCA

>H621151
GAGGTGCAGCTGGTGGAGTCTGGGGGGAGGCGTGGTCCAGCCTGGGAGGTCCCTGAGACTGTCCT
GTGCAGCGTCTGGATTCAGCTTCAGTCACTTTAACATGCACTGGGTCCGCCAGCCTCCAGGCAA
GGGGCTGGAGTGGGTGGCAGTCATACGGTATGATGCAACTAAACAGTACTATGCAGACTCCGTG
AAGGGCCGATTCTCCATCTCCAGAGACAATTCCAGGAACAATCTGCATCTGCACATGAACAGCC
TGAGAGCCGAGGACACGGCCACATATTACTGT**GCGAGAGACATATACTACGATAGCAGTGGTTC
CCGGGTCCGAGCCGCTATTGATGTC**TGGGGCCAAGGGACAATGGTCACCGTCTCTTCA

>H621162
CAGGTGCAGCTGGTGCAGTCTGGGGCTGAGATAAGAAAGCCTGGGGCCTCAGTCAAGGTCTCCT
GCAAGGCTTCTGGATACATCTTCACCGACAAATATATACACTGGGTGCGACAGGCCCCTGGACA
GGGGCTTGAGTGGATGGGATGGATCAACCCTAACATTGGCATCACAAACTATTCACAGAAATTT
CGGGGCAGGGTCACCATGACCAGGGACGCGTCCATCAACACAGCCTACATGGAGTTGAGGAGAC

Figure 10 continued

TGAAATCTGACGACACGGCCGTCTATTACTGTGCGAGAGATCTACAGGATATTATTTTGGTGGC
ACCCAATAACTTTTATCACTACTACTACATGGACGTCTGGGGCGCAGGGACCACGGTCACCGTC
TCCTCA

>H621098
GAGGTGCAGCTGGTGGAGTCTGGGGGAGGCTTGGTCCAGCCTGGGGGGTCCCTGAAACTCTCCT
GTGCAGCCTCTGGGTTCACCTTCAGTGGCTCTGCTATGCACTGGGTCCGCCAGGCTTCCGGGAA
AGGGCTGGAGTGGGTTGGCCGTATTAGAAACAAAGCTAACAGTTACGCGACAGCATATGCTGCG
TCGGTGAAAGGCAGGTTCACCATCTCCAGAGATGATTCAAAGAACACGGCGTATCTGCAAATGA
ACAGCCTGAAAACCGAGGACACGGCCGTGTATTACTGTACTAGACGGTCGGAACCTCTAGGGGA
TGATGCTTTTGATATCTGGGGCCAAGGGACAATGGTCACCGTCTCTTCAG

>H621099
GAGGTGCAGCTGGTGGAGTCTGGGGGAGGCCTGGTCAAGCCTGGGGGGTCCCTGAGACTCTCCT
GTGCAGCCTCTGGATTCACCTTCAGTAGCTATAGCATGATCTGGGTCCGCCAGGCTCCAGGGAA
GGGGCTGGAGTGGGTCTCATCCATTAGTAGGAGTAGTACTTACATGTATTACGCAGACTCAGTG
AAGGGCCGATTCACCATCTCCAGAGACAACGCCAAGAACTCACTGTATCTGCAGATGAACAGCC
TGAGAGCCGAGGACACGGCTATCTATTACTGTGCGAAGCATAATTACTATAGCAACAGCTGGTA
CGCGGAGGACTATTATTACTACTACATGGACGTCTGGGGCAAAGGGACCACGGTCACCGTCTCC
TCA

>H621178
GAGGTGCAGCTGGTGCAGTCTGGAGGAGGTGTGGTACGGCCTGGGGGGTCCCTGAGACTCTCCT
GTGCAGCCTCTGGATTCACCTTTGATGATTATGGCATGAGCTGGGTCCGCCAAGCTCCAGGGAA
GGGGCTGGAGTGGGTCTCTGGTATTAATTGGAATGGTGATAGTATAGGTTATGCAGACTCTGTG
AAGGGCCGATTCACCATCTCCAGAGACAACGCCAAGAACTCCCTGTATCTGCAAATGAACAGTC
TGAGAGCCGAGGACACGGCCTTGTATCACTGTGTGAGAGAAGGTGCTAAATCAGGTTACGATAT
TTTGACTGGTTATTACGACCCCTACTACTACTACGGTATGGACGTCTGGGGCCAAGGGACCACG
GTCACCGTCTCCTCA

>H621180
CAGGTTCAGCTGGTGCAGTCTGGAGCTGAGGTGAAGAAGCCTGGGGCCTCAGTAAAGGTCTCCT
GCAAGGCTTCTGGTTACACCTTTACCAGCTATGCTATCAGCTGGGTGCGACAGGCCCCTGGACA
AGGGCTTGAGTGGATGGGATGGATCAGCGTTAGCAATGGTAACACAAACTATGCACAGAAGCTC
CAGGGCAGAGTCACCATGACCACAGAGACATCCACGAGTACAGCCTACATGGAGCTGAGGAGCC
TGAGATCTGACGACACGGCCGTATATTATTGTGCGAGAGATGTAGGGTTCAAAACTACGACGGA
CTACTGGGGCCAGGGAACCCTGGTCACCGTCTCCTCAG

>H621182
GAGGTTCAGCTGGTGGAGTCTGGGGCTGAGGTGAAGAAGCCTGGGTCCTCGGTGAAGGTCTCCT
GCAAGGCTTCTGGAGGCACCTTCAGCAGCTATGCTATCAGCTGGGTGCGACAGGCCCCTGGACA
AGGGCTTGAGTGGATGGGAGGGATCATCCCTATCTTTGGTACAGCAAACTACGCACAGAAGTTC
CAGGGCAGAGTCACGATTACCGCGGACAAATCCACGAGCACAGCCTACATGGAGCTGAGCAGCC
TGAGATCTGAGGACACGGCCGTGTATTACTGTGCGAGTTTGTCTCAGTCGGGTGGTTATCAAAC
GTACTACTTTGACTACTGGGGCCAGGGAACCCTGGTCACCGTCTCCTCA

Figure 10 continued

>H592679
CAGGTGCAGCTGCAGGAGTCGGGCCCAGGACTGGTGAAGCCTTCACAGACCCTGTCCCTCACCT
GCGCTGTCTCTGGTGGCTCCATCAGCAGTGGTGATTCCTACTGGAGCTGGATCCGCCAGCACCC
AGGGAAGGGCCTGGAGTGGATTGGGTCCATCTATTACAGTGGGAGCACCTACTACAACCCGTCC
CTCAAGAGTCGAGTTACCATACCAATAGACACGTCTAAGAACCAGTTCTCCCTGAAGCTGAGCT
CTGTGACTGCCGCGGATACGGCCGTGTATTACTGTGCGAGACATGTTGGGGATCTGAGGGTAAA
TGATGCTTTTGATATCTGGGGCCAAGGGACAATGGTCACCGTCTCTTCAG

>H621188
GAAGTGCAGCTGGTGCAGTCTGGAGGAGGCGTGGTCCAGCCTGGGAGGTCCCTGAGACTCTCCT
GTGCAGCCTCTGGATTCACCTTCAGTAGCAATCCTATGCACTGGGTCCGCCAGGCTCCAGGCAA
GGGGCTGGAGTGGGTGGCAGTTATATCATATGATGGAAGTAATAAATACTACGCAGACTCCGTG
AAGGGCCGATTCACCATCTCCAGAGACAATTCCAAGAACACGCTGTATCTGCAAATGAACAGCC
TGAGAGCTGAGGACACGGCTGTGTATTACTGTGCGCGGGATAGCAGTGGCTGGTATTACTACCA
TAGTAGTGGCTATATTAAAGCGTTTGACTACTGGGGCCAGGGAACCCTGGTCACCGTCTCCTCA

Figure 10 continued

<u>Kappa Chain Sequences</u>
\>K620747
GAAATTGTGTTGACGCAGTCTCCAGACACCCTGTCTTTGTCTCCAGGGGAAGGAGCCACCCTCT
CCTGCAGGGCCAGCCGGACCATTACCAGCACCTACTTAGCCTGGTACCAGCAGAAACCTGGCCA
GGCTCCCAGGCTCCTCATGTATAGTGTATCCACCAGGGCCCCTGGCATCCCCGACAGGTTCAGT
GGCAGTGGGTCTGGGACAGACTTCACTCTCACCATCAGCAGACTGGAGCCTGAAGATTTTGCAG
TGTATTTCTGTCAGCAGTATGGTAGTACACCTCCGTACACTTTTGGCCAGGGGACCAAGCTGGA
GATCAGGC \>K620780
GATATTGTGATGACTCAGTCTCCACTCTCCCTGCCCGTCACCCCTGGAGAGCCGGCCTCCATCT
CCTGCAGGTCTAGTCAGAGCCTCCTGCATAGTAATGGATACAACTATTTGGATTGGTACCTGCA
GAAGCCAGGGCAGTCTCCACAGCTCCTGATCTATTTGGGTTCTAATCGGGCCTCCGGGGTCCCT
GACAGGTTCAGTGGCAGTGGATCAGGCACAGATTTTACACTGAAAATCAGCAGAGTGGAGGCTG
AGGATGTTGGGGTTTATTACTGCATGCAAGCTCTACAAACTCCGTACACTTTTGGCCAGGGGAC
CAAGCTGGAGATCAAA \>K620782
GAAATTGTGTTGACGCAGTCTCCAGCCACCCTGTCTGTGTCTCCAGGGGAAAGAGCCACCCTCT
CCTGCAGGGCCAGTCAGAGTGTTAGCAGCAACTTAGCCTGGTACCAGCAGAAACCTGGGCAGAC
TCCCAGGCTCCTCATCTATGGTGCATCCACCAGGGCCACTGGTATCCCAGCCAGGTTCAGTGGC
AGTGGGTCTGGGACAGAGTTCACTCTCACCATCAGCAGCCTGCAGTCTGAAGATTTTGCAGTTT
TTTACTGTCAGCAGTATAATAACTGGCCGCTCACTTTCGGCGGAGGGACCAAGGTGGAGATCAA
A \>K620748
GAAATAGTGATGACGCAGTCTCCAGCCACCCTGTCTGTGTCTCCAGGGGAAAGAGCCACCCTCT
CCTGCAGGGCCAGTCAGAGTGTTAGCAGCAACTTAGCCTGGTACCAGCAGAAACCTGGCCAGGC
TCCCAGGCTCCTCATCTATGGTGCATCCACCAGGGCCACTGGTATCCCAGCCAGGTTCAGTGGC
AGTGGGTCTGGGACAGAGTTCACTCTCACCATCAGCAGCCTGCAGTCTGAAGATTTTGCAGTTT
ATTACTGTCAGCAGTATAATAACTGGCCGACGTTCGGCCAAGGGACCAAGGTGGAAATCAAAC \>K620749
GAAATTGTGTTGACACAGTCTCCAGCCACCCTGTCTTTGTCTCCAGGGGAAAGAGCCACCCTCT
CCTGCAGGGCCAGTCAGGGTGTTGGCACCTACTTAGCCTGGTACCAACAGAAACCTGGCCAGGC
TCCCAGGCTCCTCATCTATGATGCATCCAACAGGGCCACTGGCATCCCAGCCAGGTTCAGTGGC
AGTGGGTCTGGGACAGACTTCACTCTCACCATCAGCAGCCTAGAGCCTGAAGATTTTGCAGTTT
ATTCCTGTCAGCAGCGTACCAACTGGCCCCTCACTTTCGGCGGAGGGACCAAGGTGGAGATCAA
GC \>K620790
GACATCCAGATGACCCAGTCTCCGTCCTCCCTGTCTGCATCTGTAGGAGACAGAGTCACCATCA
CTTGCCGGGCAAGTCAGAGCATTAGCATCTCTTTAAATTGGTATCAGCAGAAACCAGGGAAAGC
CCCCAAGCTCCTGTTTTATGGTGCATCCAATTTGCAAAGTGGGGTCCCATCAAGATTCAGTGGC
AGTGGATCTGGGACAGATTTCACTCTCACCGTTAGCAGTCTGCAACCTGAAGATTTTGCAACTT

Figure 10 continued

ACTACTGTCAACAGAGTTACAGTTCCCTGTGGACTTTTGGCCAGGGGACCAAGGTGGAGATCAA
A

>K620792
GAAATTGTGTTGACACAGTCTCCAGCCACCCTATCTTTGTCTCCAGGGGAAAGAGCCACCCTCT
CCTGCAGGGCCAGTCAGAGTGTTAGCAGCTACTTAGCCTGGTTTCAACAAAAACCTGGCCAGGC
TCCCAGGCTCCTCATCTATGATGCATCCAACAGGGCCACTGGCATCCCAGCCAGGTTCAGTGGC
AGTGGGTCTGGGACAGACTTCACTCTCACCATCAGCAGCCTAGAGCCTGAAGATTTTGCACTTT
ATTACTGTCAGCAGCGTAGCAACTGGCCTCCCATGTACACTTTTGGCCAGGGGACCAAGCTGGA
GATCAAAG

>K620793
GAAACGACACTCACGCAGTCTCCAGGCACCCTGTCTTTGTCTCCAGGGGAAAGAGCCACCCTCT
CCTGCAGGGCCAGTCAGAGTGTTAGCAGCAGCTACTTAGCCTGGTACCAGCAGAAACCTGGCCA
GGCTCCCAGGCTCCTCATCTATGGTGCATCCAGCAGGGCCACTGGCATCCCAGACAGGTTCAGT
GGCAGTGGGTCTGGGACAGACTTCACTCTCACCATCAGCAGACTGGAGCCTGAAGATTTTGCAG
TGTATTACTGTCAGCAGTATGGTAGCTCACCTCCCGTATTCACTTTCGGCCCTGGGACCAAAGT
GGATATCAAA

>K620797
GACATCCAGATGACCCAGTCTCCATCCTCCCTGTCTGCATCTGTAGGAGACAGAGTCACCATCA
GTTGCCGGGCAAGTCAGAGCATTAGCAGCAATTTAAATTGGTATCAACAGAAACCAGGGAAAGC
CCCTAAGCTCCTGATCTATGCTGCATCCAGTTTGCAAAGTGGGGTCCCATCAAGGTTCAGTGGC
AGTGGATCTGGGACAGATTTCAGTCTCACCATCAGTAGTCTGCAACCTGAAGATTTTGCAACTT
ACTACTGTCAACAGAGTTACAGTACCCCTCCCTCGACTTTTGGCCAGGGGACCAAGTTGGAGAT
CAAA

Figure 10 continued

Lambda Chain Sequences
>L620650
CAGTCTGTGTTGACTCAGCCACCCTCGGTGTCAGTGGCCCCAGGACAGACGGCCAGGATTACCT
GTGGGGCAGACAACATCGGGAGGAAAAGTGTGCACTGGTACCAGCAGAAGCCAGGCCAGGCCCC
TGTGCTGGTCGTCCACGATGATAGCGACCGGCCCTCAGGGATCTCTCAACGATTCTCTGGCTCC
AACTCTGGGAACACGGCCACCCTGACCATCAGCAGGGTCGAAGCCGGGGATGAGGCCGACTATT
ATTGTCAAATGTGGGATGTTACTCGTGATCAATATGTCTTCGGAAGTGGGACCGAGGTCACCGT
CCTA >L620584
CAGTCTGTGCTGACTCAGCCACCCTCGGTGTCTGAAGCCCCCAGGCAGAGGGTCACCATCTCCT
GTTCTGGAAGCAGCTCCAACATCGGAAATAATGCTGTAAACTGGTACCAGCAGCTCCCAGGAAA
GGCTCCCAAACTCCTCATCTATTATGATGATCTGCTGCCCTCAGGGGTCTCTGACCGATTCTCT
GGCTCCAACTCTGGCCACACGGCCACCCTGACCATCAACAGGGTCGAAGCCGGGGATGAGGCCG
ACTATTTCTGTCAGGTGTGGGACAGTAACACTGATCAATATGTCTTCGGAAATGGGACCAAGGT
CACCGTCCTAG >L620585
TCCTATGTGCTGACTCAGGAACCCTCGGTGTCAGTGGCCCCCGGACAGACGGCCAGGATTACCT
GTGGGGGAAACAACATTGGAAGAATTGTTGTGCACTGGTACCAACAGAAGCCGGGCCAGGCCCC
GGTGCTGGTCGTCCATGATGACTTCGACCGGCCCTCAGGGATCCCTGAGCGATTCTCTGGCTCC
AACTCTGGCCACACGGCCACCCTGACCATCAACAGGGTCGAAGCCGGGGATGAGGCCGACTATT
TCTGTCAGGTGTGGGACAGTAACACTGATCAATATGTCTTCGGAAATGGGACCAAGGTCACCGT
CCTAG >L620663
TCCTATGTGCTGACTCAGCCACCCTCAGTGTCAGTGGCCCCAGGAAAGACGGCCAGGATTACCT
GTGGGGGAAACAACATTGGAAGTAAAAGTGTGCACTGGTACCAGCAGAAGCCAGGCCAGGCCCC
TGTGCTGGTCATCTTTTATGATAGCAACCGGCCCTCAGGGATCCCTGAGCGATTCTCTGGCTCC
AACTCTGGGAACACGGCCACCCTGACCATCAGCAGGGTCGAGGCCGGGGATGAGGCCGACTATT
ACTGTCAGGTGTGGGATAGTAGTAGTGATCATGAGGTGTTCGGCGGAGGGACCAAACTGACCGT
CCTAG >L590920
CAGTCTGTGTTGACGCAGCCGCCCTCAGTGTCTGCGGCCCCAGGACAGAAGGTCACCATCTCCT
GCTCTGGAAGCAGCTCCAACATTGGGAATAATTTTGTATCCTGGTACCAGCGACTCCCAGGAAC
ACCCCCCAAACTCCTCATTTATGACAGTGATAAGCGACCCTCAGGGATTCCTGACCGATTCTCT
GGCTCCAAGTCTGGCACGTCAGCCACCCTGGGCATCACCGGACTCCAGACTGGGGACGAGGGCG
ATTATTACTGCGGAACATGGGATAGGAGCCTGAGTGTTGTGGTATTCGGCGGAGGGACCAAGCT
GACCGTCCTAG

Figure 10 continued

Translation of V(D)J sequences

Heavy Chain Sequences

>H621097
EVQLVESGGGLVKPGGSLRLSCVASGFTFNIYNMNWVRQAPGRGLEWVSSISLSSSYIDYADSV
EGRFTISRDNAKNSLSLQMNSLKAEDTAVYYCARGRRGEWLVLHDAFDLWGQGTLVTVSS

>H621157
EVQLVESGG.GLVQPGGSLRLSCAASGFTFSSCAMTWVRQAPGKGLEWVSVISGSGGSTYYADS
VKGRFSISRDNSKNTLYLQMNSLRAEDTAVYYCAKSWGDYYDSSGYPVYYYYYYMDVWGKGTTV
TVSS

>H621151
EVQLVESGGGVVQPGRSLRLSCAASGFSFSHFNMHWVRQPPGKGLEWVAVIRYDATKQYYADSV
KGRFSISRDNSRNNLHLHMNSLRAEDTATYYCARDIYYDSSGSRVRAAIDVWGQGTMVTVSS

>H621162
QVQLVQSGAEIRKPGASVKVSCKASGYIFTDKYIHWVRQAPGQGLEWMGWINPNIGITNYSQKF
RGRVTMTRDASINTAYMELRRLKSDDTAVYYCARDLQDIILVAPNNFYHYYYMDVWGAGTTVTV
SS

>H621098
EVQLVESGGGLVQPGGSLKLSCAASGFTFSGSAMHWVRQASGKGLEWVGRIRNKANSYATAYAA
SVKGRFTISRDDSKNTAYLQMNSLKTEDTAVYYCTRRSEPLGDDAFDIWGQGTMVTVSS

>H621099
EVQLVESGGGLVKPGGSLRLSCAASGFTFSSYSMIWVRQAPGKGLEWVSSISRSSTYMYYADSV
KGRFTISRDNAKNSLYLQMNSLRAEDTAIYYCAKHNYYSNSWYAEDYYYYYMDVWGKGTTVTVS
S

>H621178
EVQLVQSGGGVVRPGGSLRLSCAASGFTFDDYGMSWVRQAPGKGLEWVSGINWNGDSIGYADSV
KGRFTISRDNAKNSLYLQMNSLRAEDTALYHCVREGAKSGYDILTGYYDPYYYYGMDVWGQGTT
VTVSS

>H621180
QVQLVQSGAEVKKPGASVKVSCKASGYTFTSYAISWVRQAPGQGLEWMGWISVSNGNTNYAQKL
QGRVTMTTETSTSTAYMELRSLRSDDTAVYYCARDVGFKTTTDYWGQGTLVTVSS

>H621182
EVQLVESGAEVKKPGSSVKVSCKASGGTFSSYAISWVRQAPGQGLEWMGGIIPIFGTANYAQKF
QGRVTITADKSTSTAYMELSSLRSEDTAVYYCASLSQSGGYQTYYFDYWGQGTLVTVSS

Figure 10 continued

>H592679
QVQLQESGPGLVKPSQTLSLTCAVSGGSISSGDSYWSWIRQHPGKGLEWIGSIYYSGSTYYNPS
LKSRVTIPIDTSKNQFSLKLSSVTAADTAVYYCARHVGDLRVNDAFDIWGQGTMVTVSS

>H621188
EVQLVQSGGGVVQPGRSLRLSCAASGFTFSSNPMHWVRQAPGKGLEWVAVISYDGSNKYYADSV
KGRFTISRDNSKNTLYLQMNSLRAEDTAVYYCARDSSGWYYYHSSGYIKAFDYWGQGTLVTVSS

Figure 10 continued

Kappa Chain Sequences

>K620747
EIVLTQSPDTLSLSPGEGATLSCRASRTITSTYLAWYQQKPGQAPRLLMYSVSTRAPGIPDRFS
GSGSGTDFTLTISRLEPEDFAVYFCQQYGSTPPYTFGQGTKLEIR

>K620780
DIVMTQSPLSLPVTPGEPASISCRSSQSLLHSNGYNYLDWYLQKPGQSPQLLIYLGSNRASGVP
DRFSGSGSGTDFTLKISRVEAEDVGVYYCMQALQTPYTFGQGTKLEIK

>K620782
EIVLTQSPATLSVSPGERATLSCRASQSVSSNLAWYQQKPGQTPRLLIYGASTRATGIPARFSG
SGSGTEFTLTISSLQSEDFAVFYCQQYNNWPLTFGGGTKVEIK

>K620748
EIVMTQSPATLSVSPGERATLSCRASQSVSSNLAWYQQKPGQAPRLLIYGASTRATGIPARFSG
SGSGTEFTLTISSLQSEDFAVYYCQQYNNWPTFGQGTKVEIK

>K620749
EIVLTQSPATLSLSPGERATLSCRASQGVGTYLAWYQQKPGQAPRLLIYDASNRATGIPARFSG
SGSGTDFTLTISSLEPEDFAVYSCQQRTNWPLTFGGGTKVEIK

>K620790
DIQMTQSPSSLSASVGDRVTITCRASQSISISLNWYQQKPGKAPKLLFYGASNLQSGVPSRFSG
SGSGTDFTLTVSSLQPEDFATYYCQQSYSSLWTFGQGTKVEIK

>K620792
EIVLTQSPATLSLSPGERATLSCRASQSVSSYLAWFQQKPGQAPRLLIYDASNRATGIPARFSG
SGSGTDFTLTISSLEPEDFALYYCQQRSNWPPMYTFGQGTKLEIK

>K620793
ETTLTQSPGTLSLSPGERATLSCRASQSVSSSYLAWYQQKPGQAPRLLIYGASSRATGIPDRFS
GSGSGTDFTLTISRLEPEDFAVYYCQQYGSSPPVFTFGPGTKVDIK

>K620797
DIQMTQSPSSLSASVGDRVTISCRASQSISSNLNWYQQKPGKAPKLLIYAASSLQSGVPSRFSG
SGSGTDFSLTISSLQPEDFATYYCQQSYSTPPSTFGQGTKLEIK

Figure 10 continued

Lambda Chain Sequences

>L620650
QSVLTQPPSVSVAPGQTARITCGADNIGRKSVHWYQQKPGQAPVLVVHDDSDRPSGISQRFSGS
NSGNTATLTISRVEAGDEADYYCQMWDVTRDQYVFGSGTEVTVL

>L620584
QSVLTQPPSVSEAPRQRVTISCSGSSSNIGNNAVNWYQQLPGKAPKLLIYYDDLLPSGVSDRFS
GSNSGHTATLTINRVEAGDEADYFCQVWDSNTDQYVFGNGTKVTVL

>L620585
SYVLTQEPSVSVAPGQTARITCGGNNIGRIVVHWYQQKPGQAPVLVVHDDFDRPSGIPERFSGS
NSGHTATLTINRVEAGDEADYFCQVWDSNTDQYVFGNGTKVTVL

>L620663
SYVLTQPPSVSVAPGKTARITCGGNNIGSKSVHWYQQKPGQAPVLVIFYDSNRPSGIPERFSGS
NSGNTATLTISRVEAGDEADYYCQVWDSSSDHEVFGGGTKLTVL

>L590920
QSVLTQPPSVSAAPGQKVTISCSGSSSNIGNNFVSWYQRLPGTPPKLLIYDSDKRPSGIPDRFS
GSKSGTSATLGITGLQTGDEGDYYCGTWDRSLSVVVFGGGTKLTVL

TABLE 1 – Immunogenetics of Whole Zika virion-binding monoclonal antibodies

| Antibody ID | GH ID | VH | D | JH | CDR H3 length (aa) | CDR H3 sequence (aa) | H mutation frequency | Isotype |
|---|---|---|---|---|---|---|---|---|
| 119-1-D7 | H621097 | IGHV3-21*03 | 2-15*01F | IGHJ3*01 | 17 | ARGRRGEWLVLHDAFDI | 7.99% | G1 |
| 119-1-E8 | H621157 | IGHV3-23*04 | IGHD3-22*01 | IGHJ6*03 | 24 | AKSWGDYDSSGYPVYYYYYMDV | 2.43% | M |
| 119-2-F3 | H621151 | IGHV3-33*01 | IGHD3-22*01 | IGHJ3*01 | 19 | ARDIYDSSGSRVRAAIDV | 8.68% | G1 |
| 119-3-E3 | H621162 | IGHV1-2*02 | IGHD2-8*02 | IGHJ6*03 | 23 | ARDLQDILVAPNNFYHYYYMDV | 8.68% | G1 |
| 119-4-D6.01 | H621098 | IGHV3-73*01 | IGHD2-8*02 | IGHJ3*02 | 14 | TRRSEPLGDDAFDI | 0.34% | M |
| 119-4-D6.02 | H621098 | IGHV3-73*01 | IGHD2-8*02 | IGHJ3*02 | 14 | TRRSEPLGDDAFDI | 0.34% | M |
| 119-4-D6.03 | H621098 | IGHV3-73*01 | IGHD2-8*02 | IGHJ3*02 | 14 | TRRSEPLGDDAFDI | 0.34% | M |
| 119-5-C5 | H621099 | IGHV3-21*01 | IGHD6-13*01 | IGHJ6*03 | 22 | AKHNYYSNSWYAEDYYYYMDV | 2.78% | G1 |
| 120-1-D7 | H592679 | IGHV4-31*03F | IGHD7-27*01 | IGHJ3*02 | 15 | ARHVGDLRVNDAFDI | 2.41% | M |
| 120-1-G4.01 | H621180 | IGHV1-18*01 | IGHD4-17*01 | IGHJ4*02 | 12 | ARDVGFKTTTDY | 3.12% | G3 |
| 120-1-G4.02 | H621180 | IGHV1-18*01 | IGHD4-17*01 | IGHJ4*02 | 12 | ARDVGFKTTTDY | 3.12% | G3 |
| 120-1-G6 | H621182 | IGHV1-69*14 | IGHD6-13*01 | IGHJ4*02 | 16 | ASLSQSGGYQTYFDY | 0% | G1 |
| 120-2-F10 | H621188 | IGHV3-30-3*03 | IGHD3-22*01 | IGHJ4*02 | 21 | ARDSSGWYYHSSGYIKAFDY | 2.08% | G3 |
| 120-3-C3 | H621178 | IGHV3-20*01 | IGHD3-9*01 | IGHJ6*02 | 26 | VREGAKSGYDILTGYYDPYYYGMDV | 1.74 | G1 |

Figure 13

TABLE 1 – Immunogenetics of Whole Zika virion-binding monoclonal antibodies (continued)

| Antibody ID | VL ID | VL | JL | CDR L3 length (aa) | CDR L3 Sequence (aa) | Mutation frequency |
|---|---|---|---|---|---|---|
| 119-1-D7 | K620747 | IGKV3-20*01 | IGKJ2*01 | 10 | QQYGSTPPYT | 6.03% |
| 119-1-E8 | K620780 | IGKV2-28*01 | IGKJ2*01 | 9 | MQALQTPYT | 0.00% |
| 119-2-F3 | L620650 | IGLV3-21*02 | IGLJ1*01 | 11 | QMWDVTRDQYV | 5.73% |
| 119-3-E3 | K620782 | IGKV3-15*01 | IGKJ4*01 | 9 | QQYNNWPLT | 1.08% |
| 119-4-D6.01 | K620748 | IGKV3-15*01 | IGKJ1*01 | 8 | QQYNNWPT | 0% |
| 119-4-D6.02 | L620584 | IGLV1-36*01 | IGLJ1*01 | 11 | QVWDSNTDQYV | 10.20% |
| 119-4-D6.03 | L620585 | IGLV3-21*02 | IGLJ1*01 | 11 | QVWDSNTDQYV | 7.89% |
| 119-5-C5 | K620749 | IGKV3-11*01 | IGKJ4*01 | 9 | QQRTNWPLT | 1.79% |
| 120-1-D7 | L590920 | IGLV1-51*01F | IGLJ2*01 | 11 | GTWDRSLSVVV | 2.81% |
| 120-1-G4.01 | K620792 | IGKV3-11*01 | IGKJ2*01 | 11 | QQRSNWPPMYT | 1.79% |
| 120-1-G4.02 | L620663 | IGLV3-21*01 | IGLJ3*02 | 11 | QVWDSSSDHEV | 1.43% |
| 120-1-G6 | K620793 | IGKV3-20*01 | IGKJ3*01 | 11 | QQYGSSPPVFT | 2.48% |
| 120-2-F10 | K620797 | IGKV1-39*01 | IGKJ2*01 | 10 | QQSYSTPPST | 1.79% |
| 120-3-C3 | K620790 | IGKV1-39*01 | IGKJ2*01 | 9 | QQSYSSLWT | 3.94% |

Figure 13 continued

SEQUENCE LISTING

```
<160> NUMBER OF SEQ ID NOS: 74

<210> SEQ ID NO 1
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtgcagc tggtggagtc tggggggggc ctggtcaagc ctggggggtc cctgcgactc        60
tcctgtgtag cctctggatt caccttcaat atttataata tgaactgggt ccgccaggct       120
cctgggaggg ggctggaatg ggtctcatcc attagtctta gtagtagtta catagactac       180
gcagactcag tggagggccg gttcaccatc tccagagaca acgccaagaa ctcactgtct       240
ctgcaaatga acagtttgaa agccgaagac acagctgtct actactgtgc gagaggtcgc       300
cggggggagt ggctggtgct acatgatgct tttgatctct ggggccaggg gacattggtc       360
accgtctctt cag                                                          373

<210> SEQ ID NO 2
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaggtgcagc tggtggagtc tggggggggc ttggtacagc ctggggggtc cctgagactc        60
tcctgtgcag cctctggatt cacctttagc agctgtgcca tgacctgggt ccgccaggct       120
```

```
ccagggaagg ggctggagtg ggtctcagtc attagtggta gtggtggtag tacatactac       180
gcagactccg tgaagggccg gttctccatc tccagagaca attccaagaa cacgctgtat       240
ctgcaaatga acagcctgag agccgaggac acggccgtat attactgtgc gaaaagctgg       300
ggggattact atgatagtag tggttacccc gtttactact actactacta catggacgtc       360
tggggcaaag ggaccacggt caccgtctcc tca                                    393

<210> SEQ ID NO 3
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaggtgcagc tggtggagtc tggggggaggc gtggtccagc ctgggaggtc cctgagactg        60
tcctgtgcag cgtctggatt cagcttcagt cactttaaca tgcactgggt ccgccagcct       120
ccaggcaagg ggctggagtg ggtggcagtc atacggtatg atgcaactaa acagtactat       180
gcagactccg tgaagggccg attctccatc tccagagaca attccaggaa caatctgcat       240
ctgcacatga acagcctgag agccgaggac acggccacat attactgtgc gagagacata       300
tactacgata gcagtggttc ccgggtccga gccgctattg atgtctgggg ccaagggaca       360
atggtcaccg tctcttca                                                     378

<210> SEQ ID NO 4
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caggtgcagc tggtgcagtc tggggctgag ataagaaagc ctggggcctc agtcaaggtc        60
tcctgcaagg cttctggata catcttcacc gacaaatata tacactgggt gcgacaggcc       120
cctggacagg ggcttgagtg gatgggatgg atcaacccta acattggcat cacaaactat       180
tcacagaaat ttcggggcag ggtcaccatg accaggacg cgtccatcaa cacagcctac        240
atggagttga ggagactgaa atctgacgac acggccgtct attactgtgc gagagatcta       300
caggatatta ttttggtggc acccaataac ttttatcact actactacat ggacgtctgg       360
ggcgcaggga ccacggtcac cgtctcctca                                        390

<210> SEQ ID NO 5
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaggtgcagc tggtggagtc tggggggaggc ttggtccagc ctggggggtc cctgaaactc        60
tcctgtgcag cctctgggtt caccttcagt ggctctgcta tgcactgggt ccgccaggct       120
tccgggaaag ggctggagtg ggttggccgt attagaaaca aagctaacag ttacgcgaca       180
gcatatgctg cgtcggtgaa aggcaggttc accatctcca gagatgattc aaagaacacg       240
```

-continued

```
gcgtatctgc aaatgaacag cctgaaaacc gaggacacgg ccgtgtatta ctgtactaga      300
cggtcggaac tctctagggga tgatgctttt gatatctggg gccaagggac aatggtcacc      360
gtctcttcag                                                               370
```

```
<210> SEQ ID NO 6
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaggtgcagc tggtggagtc tggggggaggc ctggtcaagc ctggggggtc cctgagactc       60
tcctgtgcag cctctggatt caccttcagt agctatagca tgatctgggt ccgccaggct      120
ccagggaagg ggctggagtg ggtctcatcc attagtagga gtagtactta catgtattac      180
gcagactcag tgaagggccg attcaccatc tccagagaca acgccaagaa ctcactgtat      240
ctgcagatga acagcctgag agccgaggac acggctatct attactgtgc gaagcataat      300
tactatagca acagctggta cgcggaggac tattattact actacatgga cgtctggggc      360
aaagggacca cggtcaccgt ctcctca                                          387
```

```
<210> SEQ ID NO 7
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggtgcagc tggtgcagtc tggaggaggt gtggtacggc ctgggggggtc cctgagactc       60 tcctgtgcag cctctggatt cacctttgat gattatggca tgagctgggt ccgccaagct      120
ccagggaagg ggctggagtg ggtctctggt attaattgga atggtgatag tataggttat      180
gcagactctg tgaagggccg attcaccatc tccagagaca acgccaagaa ctccctgtat      240
ctgcaaatga acagtctgag agccgaggac acggccttgt atcactgtgt gagagaaggt      300
gctaaatcag gttacgatat tttgactggt tattacgacc cctactacta ctacggtatg      360
gacgtctggg gccaagggac cacggtcacc gtctcctca                             399
```

```
<210> SEQ ID NO 8
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
caggttcagc tggtgcagtc tggagctgag gtgaagaagc ctggggccctc agtaaaggtc       60 tcctgcaagg cttctggtta caccttntacc agctatgcta tcagctgggt gcgacaggcc      120
cctggacaag ggcttgagtg gatgggatgg atcagcgtta gcaatggtaa cacaaactat      180
gcacagaagc tccagggcag agtcaccatg accacagaga catccacgag tacagcctac      240
atggagctga ggagcctgag atctgacgac acggccgtat attattgtgc gagagatgta      300
gggttcaaaa ctacgacgga ctactggggc cagggaaccc tggtcaccgt ctcctcag       358
```

```
<210> SEQ ID NO 9
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggttcagc tggtggagtc tgggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca atccacgag cacagcctac     240 atggagctga gcagcctgag atctgaggac acggccgtgt attactgtgc gagtttgtct    300
cagtcgggtg gttatcaaac gtactacttt gactactggg gccagggaac cctggtcacc    360
gtctcctca                                                          369

<210> SEQ ID NO 10
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tgcaggagtc gggcccagga ctggtgaagc cttcacagac cctgtccctc     60
acctgcgctg tctctggtgg ctccatcagc agtggtgatt cctactggag ctggatccgc    120
cagcacccag ggaagggcct ggagtggatt gggtccatct attacagtgg gagcacctac    180
tacaacccgt ccctcaagag tcgagttacc ataccaatag acacgtctaa gaaccagttc    240
tccctgaagc tgagctctgt gactgccgcg gatacggccg tgtattactg tgcgagacat    300
gttggggatc tgagggtaaa tgatgctttt gatatctggg gccaagggac aatggtcacc    360
gtctcttcag                                                          370

<210> SEQ ID NO 11
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaagtgcagc tggtgcagtc tggaggaggc gtggtccagc ctgggaggtc cctgagactc     60
tcctgtgcag cctctggatt caccttcagt agcaatccta tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agctgaggac acggctgtgt attactgtgc gcgggatagc    300
agtggctggt attactacca tagtagtggc tatattaaag cgtttgacta ctggggccag    360
ggaaccctgg tcaccgtctc ctca                                         384

<210> SEQ ID NO 12
<211> LENGTH: 328
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gaaattgtgt tgacgcagtc tccagacacc ctgtctttgt ctccagggga aggagccacc       60
ctctcctgca gggccagccg gaccattacc agcacctact tagcctggta ccagcagaaa      120
cctggccagg ctcccaggct cctcatgtat agtgtatcca ccagggcccc tggcatcccc      180
gacaggttca gtggcagtgg gtctgggaca gacttcactc tcaccatcag cagactggag      240
cctgaagatt ttgcagtgta tttctgtcag cagtatggta gtacacctcc gtacactttt      300
ggccagggga ccaagctgga gatcaggc                                          328

<210> SEQ ID NO 13
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gatattgtga tgactcagtc tccactctcc ctgcccgtca cccctggaga gccggcctcc       60
atctcctgca ggtctagtca gagcctcctg catagtaatg gatacaacta tttggattgg      120
tacctgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttgggggtt tattactgca tgcaagctct acaaactccg      300 tacactttg gccaggggac caagctggag atcaaa                                  336

<210> SEQ ID NO 14
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gaaattgtgt tgacgcagtc tccagccacc ctgtctgtgt ctccagggga aagagccacc       60
ctctcctgca gggccagtca gagtgttagc agcaacttag cctggtacca gcagaaacct      120
gggcagactc ccaggctcct catctatggt gcatccacca gggccactgg tatcccagcc      180
aggttcagtg gcagtgggtc tgggacagag ttcactctca ccatcagcag cctgcagtct      240
gaagattttg cagttttta ctgtcagcag tataataact ggccgctcac tttcggcgga      300
gggaccaagg tggagatcaa a                                                 321

<210> SEQ ID NO 15
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaaatagtga tgacgcagtc tccagccacc ctgtctgtgt ctccagggga aagagccacc       60
```

```
ctctcctgca gggccagtca gagtgttagc agcaacttag cctggtacca gcagaaacct        120
ggccaggctc ccaggctcct catctatggt gcatccacca gggccactgg tatcccagcc        180
aggttcagtg gcagtgggtc tgggacagag ttcactctca ccatcagcag cctgcagtct        240
gaagattttg cagtttatta ctgtcagcag tataataact ggccgacgtt cggccaaggg        300
accaaggtgg aaatcaaac                                                     319
```

<210> SEQ ID NO 16
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gaaattgtgt tgacacagtc tccagccacc ctgtctttgt ctccagggga aagagccacc         60
ctctcctgca gggccagtca gggtgttggc acctacttag cctggtacca acagaaacct        120
ggccaggctc ccaggctcct catctatgat gcatccaaca gggccactgg catcccagcc        180
aggttcagtg gcagtgggtc tgggacagac ttcactctca ccatcagcag cctagagcct        240
gaagattttg cagtttattc ctgtcagcag cgtaccaact ggcccctcac tttcggcgga        300
gggaccaagg tggagatcaa gc                                                 322
```

<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gacatccaga tgacccagtc tccgtcctcc ctgtctgcat ctgtaggaga cagagtcacc         60
atcacttgcc gggcaagtca gagcattagc atctctttaa attggtatca gcagaaacca        120
gggaaagccc ccaagctcct gttttatggt gcatccaatt tgcaaagtgg ggtcccatca        180
agattcagtg gcagtggatc tgggacagat ttcactctca ccgttagcag tctgcaacct        240
gaagattttg caacttacta ctgtcaacag agttacagtt ccctgtggac ttttggccag        300
gggaccaagg tggagatcaa a                                                  321
```

<210> SEQ ID NO 18
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gaaattgtgt tgacacagtc tccagccacc ctatctttgt ctccagggga aagagccacc         60
ctctcctgca gggccagtca gagtgttagc agctacttag cctggtttca acaaaaacct        120
ggccaggctc ccaggctcct catctatgat gcatccaaca gggccactgg catcccagcc        180
aggttcagtg gcagtgggtc tgggacagac ttcactctca ccatcagcag cctagagcct        240
gaagattttg cactttatta ctgtcagcag cgtagcaact ggcctcccat gtacactttt        300
ggccagggga ccaagctgga gatcaaag                                           328
```

<210> SEQ ID NO 19
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gaaacgacac tcacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc cgtattcact     300
ttcggccctg ggaccaaagt ggatatcaaa                                       330

<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gacatccaga tgacccagtc tccatcctcc ctgtctgcat ctgtaggaga cagagtcacc      60
atcagttgcc gggcaagtca gagcattagc agcaatttaa attggtatca acagaaacca     120
gggaaagccc ctaagctcct gatctatgct gcatccagtt tgcaaagtgg ggtcccatca     180
aggttcagtg gcagtggatc tgggacagat ttcagtctca ccatcagtag tctgcaacct     240
gaagattttg caacttacta ctgtcaacag agttacagta cccctccctc gacttttggc     300
caggggacca agttggagat caaa                                             324

<210> SEQ ID NO 21
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cagtctgtgt tgactcagcc accctcggtg tcagtggccc caggacagac ggccaggatt      60
acctgtgggg cagacaacat cgggaggaaa agtgtgcact ggtaccagca gaagccaggc     120
caggcccctg tgctggtcgt ccacgatgat agcgaccggc cctcaggat c tctcaacga     180 ttctctggct ccaactctgg gaacacggcc accctgacca tcagcagggt cgaagccggg     240
gatgaggccg actattattg tcaaatgtgg gatgttactc gtgatcaata tgtcttcgga     300
agtgggaccg aggtcaccgt ccta                                             324

<210> SEQ ID NO 22
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
cagtctgtgc tgactcagcc accctcggtg tctgaagccc ccaggcagag ggtcaccatc      60
tcctgttctg gaagcagctc caacatcgga aataatgctg taaactggta ccagcagctc     120
ccaggaaagg ctcccaaact cctcatctat tatgatgatc tgctgccctc aggggtctct     180
gaccgattct ctggctccaa ctctggccac acggccaccc tgaccatcaa cagggtcgaa     240 gccgggatg aggccgacta tttctgtcag gtgtgggaca gtaacactga tcaatatgtc      300
ttcggaaatg ggaccaaggt caccgtccta g                                     331
```

```
<210> SEQ ID NO 23
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tcctatgtgc tgactcagga accctcggtg tcagtggccc ccggacagac ggccaggatt      60
acctgtgggg gaaacaacat tggaagaatt gttgtgcact ggtaccaaca gaagccgggc     120
caggccccgg tgctggtcgt ccatgatgac ttcgaccggc cctcaggat ccctgagcga      180 ttctctggct ccaactctgg ccacacggcc accctgacca tcaacagggt cgaagccggg     240
gatgaggccg actatttctg tcaggtgtgg gacagtaaca ctgatcaata tgtcttcgga     300
aatgggacca aggtcaccgt cctag                                            325
```

```
<210> SEQ ID NO 24
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tcctatgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat cttttatgat agcaaccggc cctcaggat ccctgagcga      180 ttctctggct ccaactctgg gaacacggcc accctgacca tcagcagggt cgaggccggg     240
gatgaggccg actattactg tcaggtgtgg gatagtagta gtgatcatga ggtgttcggc     300
ggagggacca aactgaccgt cctag                                            325
```

```
<210> SEQ ID NO 25
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cagtctgtgt tgacgcagcc gccctcagtg tctgcggccc caggacagaa ggtcaccatc      60
tcctgctctg gaagcagctc caacattggg aataattttg tatcctggta ccagcgactc     120
ccaggaacac cccccaaact cctcatttat gacagtgata agcgaccctc agggattcct     180
gaccgattct ctggctccaa gtctggcacg tcagccaccc tgggcatcac cggactccag     240 actgggacg agggcgatta ttactgcgga acatgggata ggagcctgag tgttgtggta     300
```
ttcggcggag ggaccaagct gaccgtccta g                                          331

<210> SEQ ID NO 26
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Asn Ile Tyr
            20                  25                  30

Asn Met Asn Trp Val Arg Gln Ala Pro Gly Arg Gly Leu Glu Trp Val
        35                  40                  45

Ser Ser Ile Ser Leu Ser Ser Ser Tyr Ile Asp Tyr Ala Asp Ser Val
    50                  55                  60

Glu Gly Arg Phe Thr Ile Ser Arg Asp Asn Ala Lys Asn Ser Leu Ser
65                  70                  75                  80

Leu Gln Met Asn Ser Leu Lys Ala Glu Asp Thr Ala Val Tyr Tyr Cys
                85                  90                  95

Ala Arg Gly Arg Arg Gly Glu Trp Leu Val Leu His Asp Ala Phe Asp
            100                 105                 110

Leu Trp Gly Gln Gly Thr Leu Val Thr Val Ser Ser
        115                 120

<210> SEQ ID NO 27
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Cys
            20                  25                  30

Ala Met Thr Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Gly Asp Tyr Tyr Asp Ser Ser Gly Tyr Pro Val Tyr
            100                 105                 110

Tyr Tyr Tyr Tyr Tyr Met Asp Val Trp Gly Lys Gly Thr Thr Val Thr
        115                 120                 125

Val Ser Ser
    130

<210> SEQ ID NO 28
<211> LENGTH: 126

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser His Phe
            20                  25                  30

Asn Met His Trp Val Arg Gln Pro Pro Gly Lys Gly Leu Glu Trp Val
        35                  40                  45

Ala Val Ile Arg Tyr Asp Ala Thr Lys Gln Tyr Tyr Ala Asp Ser Val
    50                  55                  60

Lys Gly Arg Phe Ser Ile Ser Arg Asp Asn Ser Arg Asn Asn Leu His
65                  70                  75                  80

Leu His Met Asn Ser Leu Arg Ala Glu Asp Thr Ala Thr Tyr Tyr Cys
                85                  90                  95

Ala Arg Asp Ile Tyr Tyr Asp Ser Ser Gly Ser Arg Val Arg Ala Ala
            100                 105                 110

Ile Asp Val Trp Gly Gln Gly Thr Met Val Thr Val Ser Ser
            115                 120                 125

<210> SEQ ID NO 29
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Ile Arg Lys Pro Gly Ala
1               5                   10                  15

Ser Val Lys Val Ser Cys Lys Ala Ser Gly Tyr Ile Phe Thr Asp Lys
            20                  25                  30

Tyr Ile His Trp Val Arg Gln Ala Pro Gly Gln Gly Leu Glu Trp Met
        35                  40                  45

Gly Trp Ile Asn Pro Asn Ile Gly Ile Thr Asn Tyr Ser Gln Lys Phe
    50                  55                  60

Arg Gly Arg Val Thr Met Thr Arg Asp Ala Ser Ile Asn Thr Ala Tyr
65                  70                  75                  80

Met Glu Leu Arg Arg Leu Lys Ser Asp Asp Thr Ala Val Tyr Tyr Cys
                85                  90                  95

Ala Arg Asp Leu Gln Asp Ile Ile Leu Val Ala Pro Asn Asn Phe Tyr
            100                 105                 110

His Tyr Tyr Tyr Met Asp Val Trp Gly Ala Gly Thr Thr Val Thr Val
            115                 120                 125

Ser Ser
    130

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 30

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Asn Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Arg Ser Glu Pro Leu Gly Asp Asp Ala Phe Asp Ile
            100                 105                 110

Trp Gly Gln Gly Thr Met Val Thr Val Ser Ser
        115                 120
```

<210> SEQ ID NO 31
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
        35                  40                  45

Ser Ser Ile Ser Arg Ser Ser Thr Tyr Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Lys His Asn Tyr Tyr Ser Asn Ser Trp Tyr Ala Glu Asp Tyr Tyr
            100                 105                 110

Tyr Tyr Tyr Met Asp Val Trp Gly Lys Gly Thr Thr Val Thr Val Ser
        115                 120                 125

Ser
```

<210> SEQ ID NO 32
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Glu Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30
```

-continued

```
Gly Met Ser Trp Val Arg Gln Ala Pro Gly Lys Gly Leu Glu Trp Val
        35                  40                  45

Ser Gly Ile Asn Trp Asn Gly Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Val Arg Glu Gly Ala Lys Ser Gly Tyr Asp Ile Leu Thr Gly Tyr Tyr
                100                 105                 110

Asp Pro Tyr Tyr Tyr Tyr Gly Met Asp Val Trp Gly Gln Gly Thr Thr
        115                 120                 125

Val Thr Val Ser Ser
    130
```

```
<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile Ser Trp Val Arg Gln Ala Pro Gly Gln Gly Leu Glu Trp Met
        35                  40                  45

Gly Trp Ile Ser Val Ser Asn Gly Asn Thr Asn Tyr Ala Gln Lys Leu
    50                  55                  60

Gln Gly Arg Val Thr Met Thr Thr Glu Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gly Phe Lys Thr Thr Thr Asp Tyr Trp Gly Gln Gly
                100                 105                 110

Thr Leu Val Thr Val Ser Ser
        115
```

```
<210> SEQ ID NO 34
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Ser Gln Ser Gly Gly Tyr Gln Thr Tyr Tyr Phe Asp Tyr
            100                 105                 110

Trp Gly Gln Gly Thr Leu Val Thr Val Ser Ser
        115                 120

<210> SEQ ID NO 35
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
                20                  25                  30

Asp Ser Tyr Trp Ser Trp Ile Arg Gln His Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Pro Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Val Gly Asp Leu Arg Val Asn Asp Ala Phe Asp Ile
            100                 105                 110

Trp Gly Gln Gly Thr Met Val Thr Val Ser Ser
        115                 120

<210> SEQ ID NO 36
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Asn
                20                  25                  30

Pro Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Gly Trp Tyr Tyr Tyr His Ser Ser Gly Tyr Ile
            100                 105                 110
```

-continued

```
Lys Ala Phe Asp Tyr Trp Gly Gln Gly Thr Leu Val Thr Val Ser Ser
        115                 120                 125

<210> SEQ ID NO 37
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Leu Thr Gln Ser Pro Asp Thr Leu Ser Leu Ser Pro Gly
1               5                   10                  15

Glu Gly Ala Thr Leu Ser Cys Arg Ala Ser Arg Thr Ile Thr Ser Thr
            20                  25                  30

Tyr Leu Ala Trp Tyr Gln Gln Lys Pro Gly Gln Ala Pro Arg Leu Leu
        35                  40                  45

Met Tyr Ser Val Ser Thr Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Ser Thr Pro
                85                  90                  95

Pro Tyr Thr Phe Gly Gln Gly Thr Lys Leu Glu Ile Arg
            100                 105

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

-continued

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Thr Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Phe Tyr Cys Gln Gln Tyr Asn Asn Trp Pro Leu
                85                  90                  95

Thr Phe Gly Gly Gly Thr Lys Val Glu Ile Lys
            100                 105
```

```
<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Gln Gly Thr Lys Val Glu Ile Lys
            100                 105
```

```
<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Gly Thr Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Ser Cys Gln Gln Arg Thr Asn Trp Pro Leu
                85                  90                  95

Thr Phe Gly Gly Gly Thr Lys Val Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Ser
            20                  25                  30

Leu Asn Trp Tyr Gln Gln Lys Pro Gly Lys Ala Pro Lys Leu Leu Phe
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Ser Leu Trp
                85                  90                  95

Thr Phe Gly Gln Gly Thr Lys Val Glu Ile Lys
            100                 105

<210> SEQ ID NO 43
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Ser Asn Trp Pro Pro
                85                  90                  95

Met Tyr Thr Phe Gly Gln Gly Thr Lys Leu Glu Ile Lys
            100                 105

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 44

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Val Phe Thr Phe Gly Pro Gly Thr Lys Val Asp Ile Lys
            100                 105                 110
```

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 45

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Ser Asn
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ser Thr Phe Gly Gln Gly Thr Lys Leu Glu Ile Lys
            100                 105
```

<210> SEQ ID NO 46
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 46

```
Gln Ser Val Leu Thr Gln Pro Pro Ser Val Ser Val Ala Pro Gly Gln
1               5                   10                  15

Thr Ala Arg Ile Thr Cys Gly Ala Asp Asn Ile Gly Arg Lys Ser Val
                20                  25                  30

His Trp Tyr Gln Gln Lys Pro Gly Gln Ala Pro Val Leu Val Val His
            35                  40                  45

Asp Asp Ser Asp Arg Pro Ser Gly Ile Ser Gln Arg Phe Ser Gly Ser
        50                  55                  60

Asn Ser Gly Asn Thr Ala Thr Leu Thr Ile Ser Arg Val Glu Ala Gly
```

```
65              70              75              80

Asp Glu Ala Asp Tyr Tyr Cys Gln Met Trp Asp Val Thr Arg Asp Gln
                85              90              95

Tyr Val Phe Gly Ser Gly Thr Glu Val Thr Val Leu
            100             105

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ser Val Leu Thr Gln Pro Pro Ser Val Ser Glu Ala Pro Arg Gln
1               5               10              15

Arg Val Thr Ile Ser Cys Ser Gly Ser Ser Ser Asn Ile Gly Asn Asn
                20              25              30

Ala Val Asn Trp Tyr Gln Gln Leu Pro Gly Lys Ala Pro Lys Leu Leu
            35              40              45

Ile Tyr Tyr Asp Asp Leu Leu Pro Ser Gly Val Ser Asp Arg Phe Ser
        50              55              60

Gly Ser Asn Ser Gly His Thr Ala Thr Leu Thr Ile Asn Arg Val Glu
65              70              75              80

Ala Gly Asp Glu Ala Asp Tyr Phe Cys Gln Val Trp Asp Ser Asn Thr
                85              90              95

Asp Gln Tyr Val Phe Gly Asn Gly Thr Lys Val Thr Val Leu
            100             105             110

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Tyr Val Leu Thr Gln Glu Pro Ser Val Ser Val Ala Pro Gly Gln
1               5               10              15

Thr Ala Arg Ile Thr Cys Gly Gly Asn Asn Ile Gly Arg Ile Val Val
                20              25              30

His Trp Tyr Gln Gln Lys Pro Gly Gln Ala Pro Val Leu Val Val His
            35              40              45

Asp Asp Phe Asp Arg Pro Ser Gly Ile Pro Glu Arg Phe Ser Gly Ser
        50              55              60

Asn Ser Gly His Thr Ala Thr Leu Thr Ile Asn Arg Val Glu Ala Gly
65              70              75              80

Asp Glu Ala Asp Tyr Phe Cys Gln Val Trp Asp Ser Asn Thr Asp Gln
                85              90              95

Tyr Val Phe Gly Asn Gly Thr Lys Val Thr Val Leu
            100             105

<210> SEQ ID NO 49
<211> LENGTH: 108
<212> TYPE: PRT
<213> ORGANISM: Artificial Sequence
<220> FEATURE:
<223> OTHER INFORMATION: Description of Artificial Sequence: Synthetic
```

-continued

```
        polypeptide

<400> SEQUENCE: 49

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Phe
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Glu Val Phe Gly Gly Gly Thr Lys Leu Thr Val Leu
            100                 105

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Arg Leu Pro Gly Thr Pro Pro Lys Leu Leu
        35                  40                  45

Ile Tyr Asp Ser Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Gly Asp Tyr Tyr Cys Gly Thr Trp Asp Arg Ser Leu
                85                  90                  95

Ser Val Val Val Phe Gly Gly Gly Thr Lys Leu Thr Val Leu
            100                 105                 110

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Gly Arg Arg Gly Glu Trp Leu Val Leu His Asp Ala Phe Asp
1               5                   10                  15

Leu

<210> SEQ ID NO 52
<211> LENGTH: 24
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 52

Ala Lys Ser Trp Gly Asp Tyr Tyr Asp Ser Ser Gly Tyr Pro Val Tyr
1               5                   10                  15

Tyr Tyr Tyr Tyr Tyr Met Asp Val
            20

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Asp Ile Tyr Tyr Asp Ser Ser Gly Ser Arg Val Arg Ala Ala
1               5                   10                  15

Ile Asp Val

<210> SEQ ID NO 54
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Arg Asp Leu Gln Asp Ile Ile Leu Val Ala Pro Asn Asn Phe Tyr
1               5                   10                  15

His Tyr Tyr Tyr Met Asp Val
            20

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Arg Arg Ser Glu Pro Leu Gly Asp Asp Ala Phe Asp Ile
1               5                   10

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Lys His Asn Tyr Tyr Ser Asn Ser Trp Tyr Ala Glu Asp Tyr Tyr
1               5                   10                  15

Tyr Tyr Tyr Met Asp Val
            20

<210> SEQ ID NO 57
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 57

Ala Arg His Val Gly Asp Leu Arg Val Asn Asp Ala Phe Asp Ile
1               5                   10                  15

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Arg Asp Val Gly Phe Lys Thr Thr Thr Asp Tyr
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ser Leu Ser Gln Ser Gly Gly Tyr Gln Thr Tyr Tyr Phe Asp Tyr
1               5                   10                  15

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Arg Asp Ser Ser Gly Trp Tyr Tyr Tyr His Ser Ser Gly Tyr Ile
1               5                   10                  15

Lys Ala Phe Asp Tyr
            20

<210> SEQ ID NO 61
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Arg Glu Gly Ala Lys Ser Gly Tyr Asp Ile Leu Thr Gly Tyr Tyr
1               5                   10                  15

Asp Pro Tyr Tyr Tyr Tyr Gly Met Asp Val
            20                  25

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic

```
peptide

<400> SEQUENCE: 62

Gln Gln Tyr Gly Ser Thr Pro Pro Tyr Thr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Gln Ala Leu Gln Thr Pro Tyr Thr
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Met Trp Asp Val Thr Arg Asp Gln Tyr Val
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Tyr Asn Asn Trp Pro Leu Thr
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Tyr Asn Asn Trp Pro Thr
1               5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Val Trp Asp Ser Asn Thr Asp Gln Tyr Val
1               5                   10

<210> SEQ ID NO 68
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Arg Thr Asn Trp Pro Leu Thr
1               5

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Thr Trp Asp Arg Ser Leu Ser Val Val Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Arg Ser Asn Trp Pro Pro Met Tyr Thr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Val Trp Asp Ser Ser Ser Asp His Glu Val
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Tyr Gly Ser Ser Pro Pro Val Phe Thr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73
```

-continued

```
Gln Gln Ser Tyr Ser Thr Pro Pro Ser Thr
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Ser Tyr Ser Ser Leu Trp Thr
1               5
```

ZIKA ANTIBODIES AND THEIR USE

This application claims the benefit of and priority to U.S. Patent Application Ser. No. 62/900,201 filed Sep. 13, 2019 which content is incorporated by reference in its entirety.

SEQUENCE LISTING

The instant application contains a Sequence Listing which has been submitted electronically in ASCII format and is hereby incorporated by reference in its entirety. Said ASCII copy, created on Jul. 11, 2025, is named 1234300_00353WO1_SL-jgc.txt and is 52,525 bytes in size.

This invention was made with government support under R21-AI132677 awarded by National Institute of Allergy & Infectious Diseases (NIH/NIAID). The government has certain rights in the invention.

TECHNICAL FIELD

The invention relates to human antibodies binding to and neutralizing Zika virus (ZIKV) and their uses.

BACKGROUND

Human infection with ZIKA virus (ZIKV), a mosquito-borne flavivirus, has spread rapidly since the 2015 outbreak in Brazil, and the World Health Organization declared ZIKV infection an International Public Health Emergency in 2016 (Fauci and Morens, N Engl J Med 2016 Feb. 18; 374(7): 601-4; Heymann et al., 2016; Petersen et al., 2016). ZIKV was discovered in 1947 (Driggers et al., 2016a) and, although it had previously caused only sporadic disease in Africa and Asia, more recent outbreaks occurred in Micronesia in 2007 and in French Polynesia in 2013 (Broutet et al., 2016). ZIKV infection has been identified as the etiological agent of severe neurological defects, including microcephaly during fetal development (Driggers et al., N Engl J Med 2016 Jun. 2; 374(22):2142-51) and neuronal injury associated with Guillain-Barre syndrome in adults (Dejni-rattisai et al., 2016).

New modes of viral transmission, including maternal-fetal (Brasil et al., N Engl J Med 2016; 375:2321-2334) and sexual transmission (Hills et al., MMWR Morb Mortal Wkly Rep 2016; 65:215-216), have been reported. ZIKV can infect human skin explants, peripheral blood mononuclear cells, human neuroprogenitor cells, and human cerebral organoids (Dang et al., 2016a; Hamel et al., 2015; Tang et al., 2016). In mouse models, ZIKV may be neurotropic (Cugola et al., 2016 *Nature* 534, 267-271 (2016); Lazear et al., 2016 Cell Host Microbe 2016 May 11; 19(5):720-30; Li et al., 2016; Mlakar et al., 2016; Sarno et al., 2016).

ZIKV and other members of the Flaviviridae family, such as dengue (DENV), West Nile (WNV), yellow fever (YFV), and Japanese encephalopathy (JEV), are positive (+) single-stranded RNA viruses. The ZIKV genome encodes a single polyprotein precursor that is cleaved by viral and host proteases to produce three structural and seven nonstructural proteins.

Although our understanding of the molecular mechanisms involved in ZIKV infection of human cells has increased dramatically in the past few years, key determinants of ZIKV pathogenicity, such as cell-type specificity, mode of entry, and host factors essential for replication, are still largely unknown. In particular, there is a need for effective therapeutic and/or prophylactic measures against Zika infection.

SUMMARY

In one aspect the invention provides antibodies or antigen-binding fragments thereof that specifically bind to Zika virus, and neutralize Zika virus. The antibodies and fragments of the invention do not bind to Dengue virus serotypes 1-4. In non-limiting embodiment, the antibody of the invention is IgM. In other aspects, the invention provides immortalized B cells that produce such antibodies and antibody fragments.

In other aspects, the invention provides nucleic acids that encode the antibodies or antibody fragments of the invention. In non-limiting embodiments, these nucleic acids are mRNA, modified or unmodified. In non-limiting embodiments these mRNAs are formulated with lipid nanoparticles (LNP) suitable for therapeutic delivery.

In addition, the invention relates to the use of the antibodies and antibody fragments of the invention in screening methods as well as in the diagnosis, prophylaxis and treatment of ZIKV infection.

In one embodiment, the invention provides a recombinant Zika antibody, or an antigen-binding fragment thereof, wherein in certain non-limiting embodiments the antibody or fragment thereof specifically binds to a Zika virus and neutralizes Zika virus infection. In certain embodiments, the antibody specifically binds to a Zika virus epitope. In certain embodiments, the antibody, or the antigen-binding fragment thereof, wherein the concentration of the antibody, or antigen-binding fragment thereof, required for 50% neutralization of Zika virus (IC50) is as described in Ex. 1. In certain embodiments, the IC50 is up to about 1 µg/ml, up to about 500 ng/ml, up to about 250 ng/ml, up to about 100 ng/ml or up to about 50 ng/ml.

In certain embodiments, the antibody, or antigen-binding fragment thereof, does not have detectable binding, i.e., essentially does not bind, to Dengue virus-like particles and/or to Dengue envelope protein.

In certain embodiments, the antibody, or the antigen-binding fragment thereof, does not contribute to antibody-dependent enhancement of Zika virus infection.

In certain embodiments, the antibody, or the antigen-binding fragment thereof is a fully human antibody.

In certain embodiments, the antibody, or the antigen-binding fragment thereof, is a recombinantly produced human monoclonal antibody.

In certain embodiments, the antibody, or the antigen-binding fragment thereof, comprises an Fc moiety. In certain embodiments, the antibody or fragment thereof is any isotype. In certain embodiments, the antibody or fragment thereof is IgM. In certain embodiments, the antibody or fragment thereof is IgG.

In certain embodiments, the Fc moiety comprises a mutation, wherein the mutation could cause reducing binding of the antibody to an Fc receptor. In certain embodiments, the antibody, or antigen-binding fragment thereof, comprises a CH2 L4A mutation, a CH2 L5A mutation, or both. See U.S. Patent Publication No. 20190256582 incorporated by reference in its entirety.

In certain embodiments, the invention provides a recombinant Zika antibody or the antigen-binding fragment thereof, as described in Ex. 1, Table 2, or FIG. 10.

In certain embodiments, the antibody, or the antigen-binding fragment thereof comprises a heavy chain (VH) comprising at least one CDRH, i.e. CDRH1, CDRH2 and CDRH3 and a light chain (VL) comprising at least one CDRL, i.e. CDRL1, CDRL2 and CDRL3, wherein at the least one CDR, comprises, consists essentially of, or consists of an amino acid sequence according to any of the CDR sequences listed in FIG. 10, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. In certain embodiments, the functional sequence variant has 80%, 81%, 82%, 83%, 84%, 85%, 86%, 87%, 88%, 89%, 90%, 91%, 92%, 93%, 94%, 95%, 96%, 97%, 98% or 99% identity to any of the sequences listed in FIG. 10.

In certain embodiments, the antibody, or the antigen-binding fragment thereof comprises a heavy chain comprising CDRH1, CDRH2 and CDRH3 and a light chain comprising CDRL1, CDRL2 and CDRL3, wherein at least one CDR, comprises, consists essentially of or consists of an amino acid sequence according to any of the CDR sequences in FIG. 10, including without limitation CDR sequences of VH H592679 or of VL L590920 in FIG. 10, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. In certain embodiments, the functional sequence variant has 80%, 81%, 82%, 83%, 84%, 85%, 86%, 87%, 88%, 89%, 90%, 91%, 92%, 93%, 94%, 95%, 96%, 97%, 98% or 99% identity to any of the sequences listed in FIG. 10.

In certain embodiments, the antibody, or the antigen-binding fragment thereof comprises, consists essentially of, or consists of a VH amino acid sequence VH H592679 or a VL amino acid sequence VL L590920 in FIG. 10 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. In certain embodiments the functional sequence variant has 80%, 81%, 82%, 83%, 84%, 85%, 86%, 87%, 88%, 89%, 90%, 91%, 92%, 93%, 94%, 95%, 96%, 97%, 98% or 99% identity to any of the sequences listed in FIG. 10.

In certain embodiments, the antibody, or the antigen-binding fragment thereof comprises, consists essentially of, or consists of a VH amino acid sequence according to VH H592679 or a VL amino acid sequence according to VL L590920 in FIG. 10. In certain embodiments, the antibody or antigen binding fragment thereof, comprises, consists essentially of, or consists of a VH amino acid sequence according to VH H592679 and a VL amino acid sequence according to VL L590920 in FIG. 10.

In certain embodiments, the antibody is DH1017.IgM or DH1017.IgG.

In certain embodiments, the antibody, or the antigen-binding fragment thereof is a purified antibody, a single chain antibody, a Fab, a Fab', a F(ab')2, a Fv or a scFv.

In certain embodiments, the Zika antibody is IgM or IgG isotype.

In certain aspects, the antibody, or the antigen-binding fragment thereof, is for use as a medicament.

In certain embodiments, the antibody, or the antigen-binding fragment thereof, is for use in the prevention and/or treatment of Zika virus infection.

In certain aspects, the invention provides a nucleic acid molecule comprising a polynucleotide encoding the antibody, or the antigen-binding fragment thereof.

In certain embodiments, the polynucleotide sequence comprises, consists essentially of, or consists of a nucleic acid sequence according to any one of the sequences in FIG. 10; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. In certain embodiments, the functional sequence variant has 80%. 81%, 82%, 83%, 84%, 85%, 86%, 87%, 88%, 89%, 90%, 91%, 92%, 93%, 94%, 95%, 96%, 97%, 98% or 99% identity to any one of the sequences in FIG. 10.

In certain embodiments, the nucleic acid is an mRNA, wherein in certain embodiments the mRNA is suitable for use and delivery as a therapeutic mRNA. In certain embodiments, the mRNA is a modified mRNA, which could be suitable for a therapeutic use.

In certain embodiments, the invention provides a vector comprising the nucleic acid molecule encoding an antibody of the invention or a fragment thereof.

In certain aspects, the invention provides a cell expressing the antibody, or the antigen-binding fragment thereof. In certain embodiments, the cell comprises a vector comprising the nucleic acid molecule encoding an antibody of the invention or a fragment thereof.

In certain aspects, the invention provides a pharmaceutical composition comprising an antibody of the invention, or the antigen-binding fragment thereof, a nucleic acid encoding an antibody of the invention, or the antigen-binding fragment thereof. In certain embodiments, the nucleic acid is an mRNA, modified or unmodified.

In certain embodiments, the pharmaceutical composition further comprises a pharmaceutically acceptable excipient, diluent or carrier.

In certain aspects, the invention provides a method of treating or preventing Zika infection in a subject in need thereof, comprising administering a pharmaceutical composition, in an amount and under a treatment schedule suitable to effect treatment or prevention, the method comprising administering a recombinant Zika antibody of the invention or a fragment thereof. In certain aspects, the invention provides a method of treating or preventing Zika infection in a subject in need thereof, comprising administering a pharmaceutical composition, in an amount and under a treatment schedule suitable to effect treatment or prevention, the method comprising administering a nucleic acid encoding the recombinant Zika antibody of the invention or a fragment thereof, optionally in a vector, in an amount suitable to effect treatment or prevention of Zika infection.

In certain embodiments, the subject of the invention is pregnant or expected to become pregnant. In certain embodiments, the antibody protects against mother to child transmission of the Zika virus.

5 through EBV transformation and stimulation in culture. The first bar (left most side in the figure) shows IgM culture. The rest of the bars show IgG cultures.

Figure 4A:
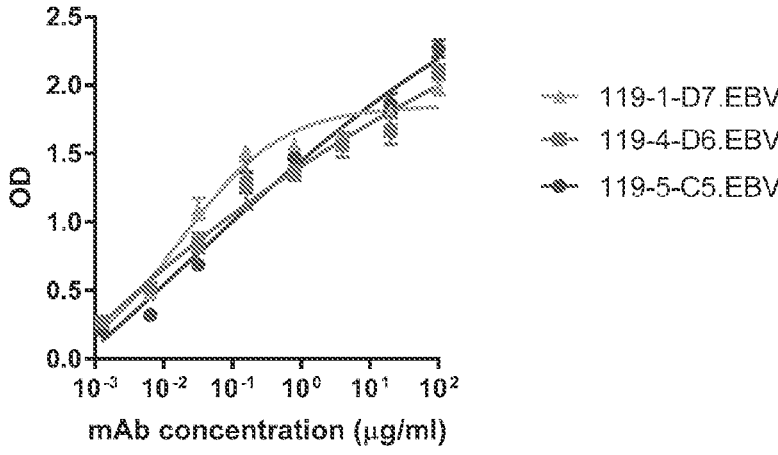
Figure 4B:
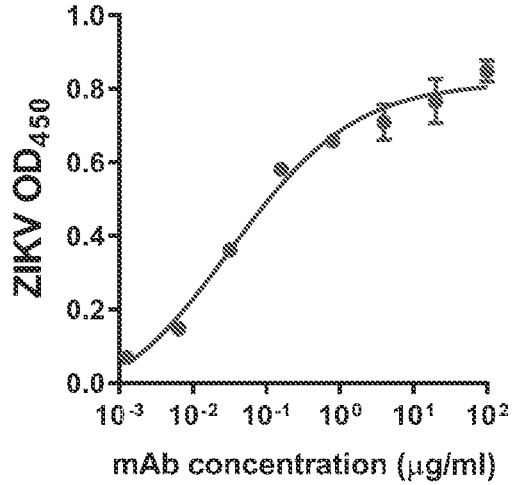

FIGS. 4A and 4B show purified monoclonal antibody binding to ZIKV. Titration of monoclonal antibodies binding to whole ZIKV from ARB34 (4A top) and ARB73 (4B bottom).

Figure 5A:
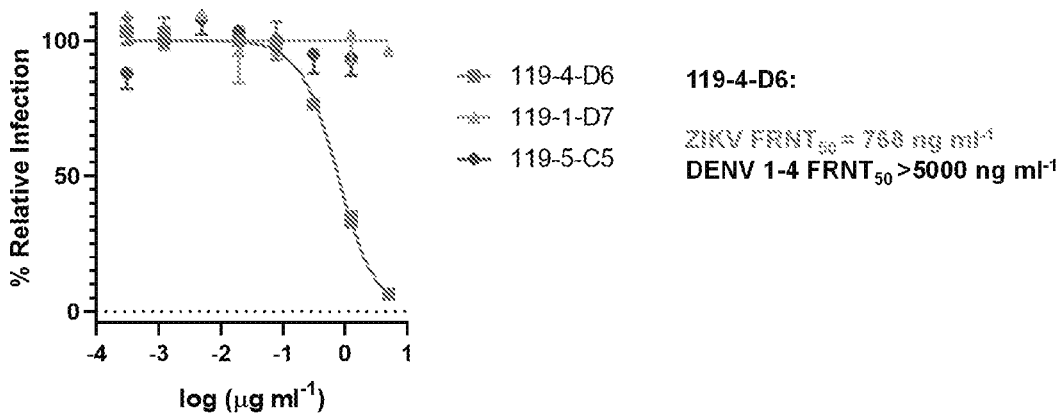
Figure 5B:
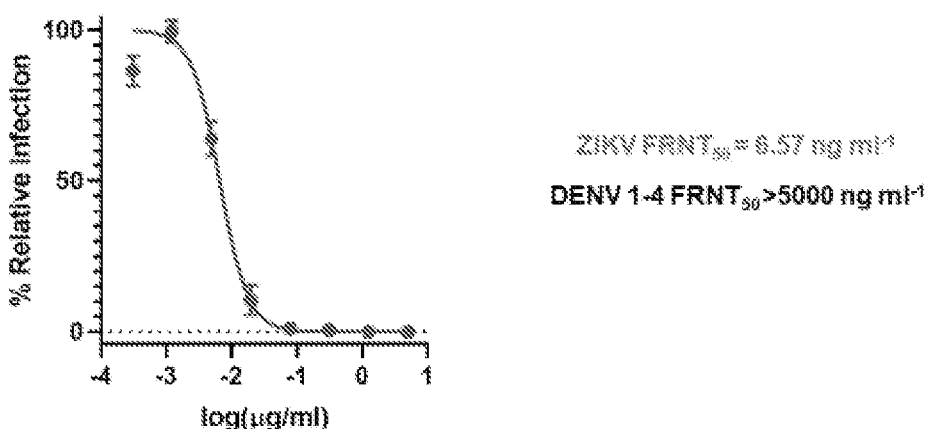

FIGS. 5A and 5B show neutralization assays. Neutralizing activity of mAbs 119-4-D6, 119-1-D7, 119-5-C5 (5A top) and 120-1-D7 (5B bottom) was measured and corresponding methods are described in Singh T et al. PLoS Negl Trop Dis 2019 Aug. 26; 13(8):e0007648, PMID 31449521.

Figure 6:
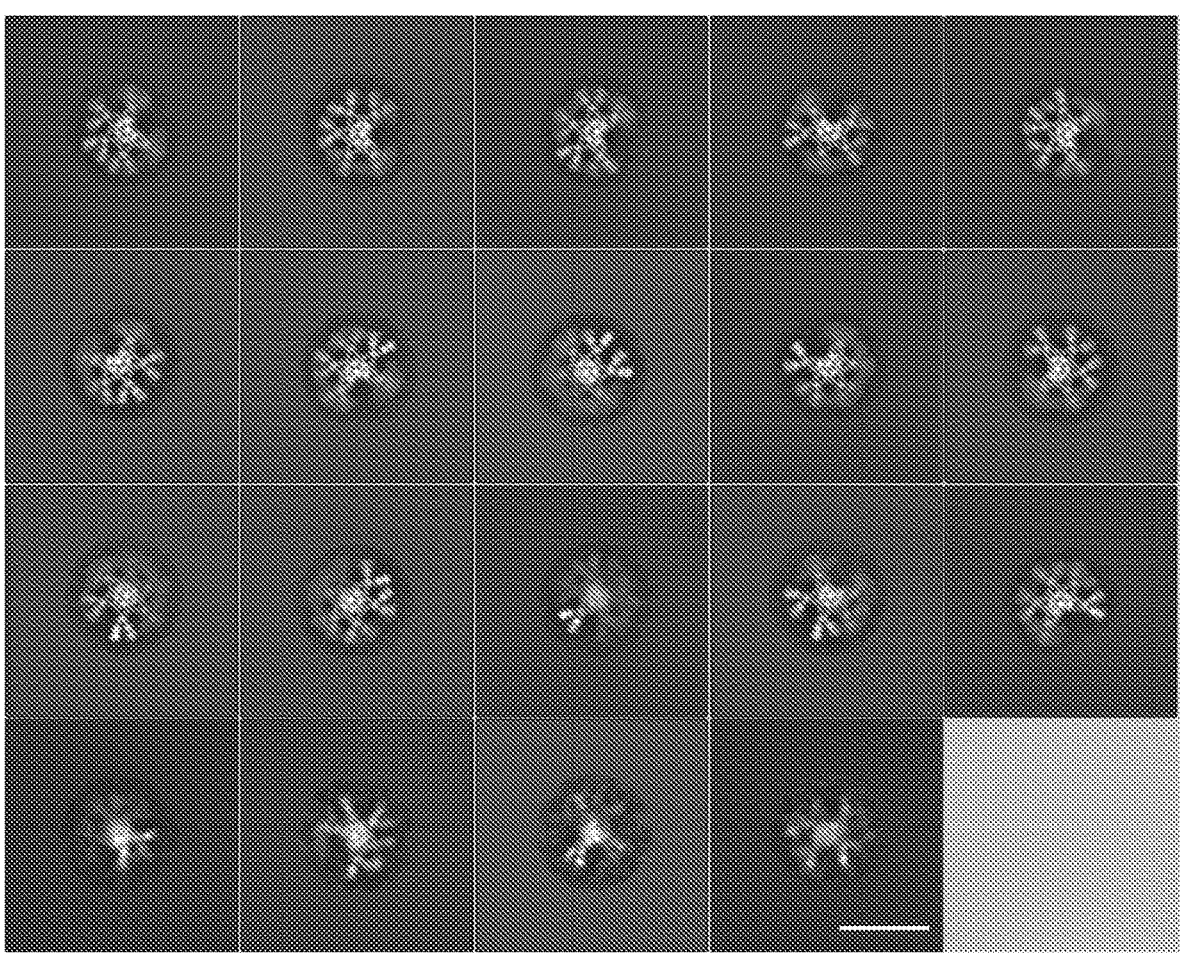

FIG. 6 shows DH1017.IgM (120-1-D7) class averages. Negative stain electron microscopy images of DH1017.IgM monoclonal antibody. Scale bar at the lower right is 40 nm (white bar). Class averages are arranged from most populated to least populated, left to right and top to bottom.

Figure 7:
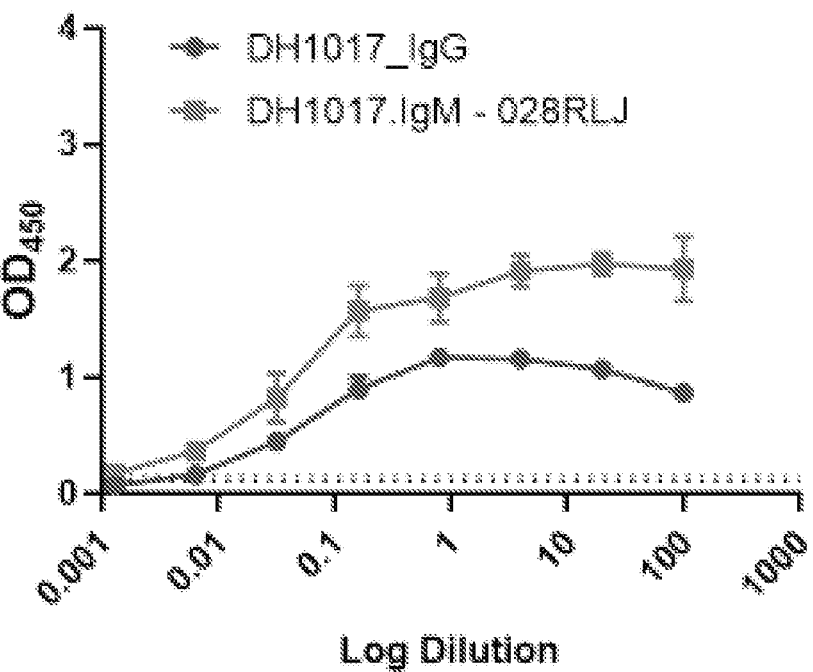
Figure 7:

FIG. 7 shows DH1017.IgG and DH1017.IgM binding to ZIKV. DH1017.IgG and DH1017.IgM monoclonal antibodies were tested for binding to whole ZIKV using starting concentrations of 100 ug/ml with 5-fold serial dilutions used to generate a binding curve. DH1017.IgG is shown in circles and DH1017.IgM is shown in squares.

Figure 8:
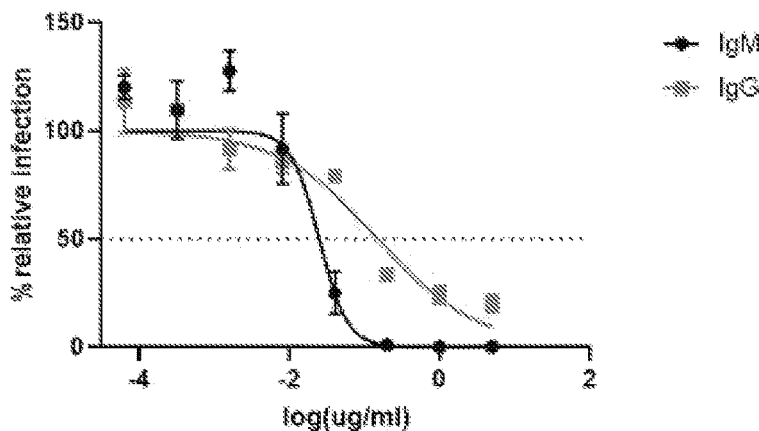

FIG. 8 shows ZIKV neutralization of DH1017.IgM and DH1017.IgG. DH1017.IgM is shown in circles and DH1017.IgG is shown in squares. FRNT50 is reported both in ng/ml and pM. Curves indicate the optimal non-linear sigmoidal fit to the data and are used to calculate the FRNT50.

Figure 9A:
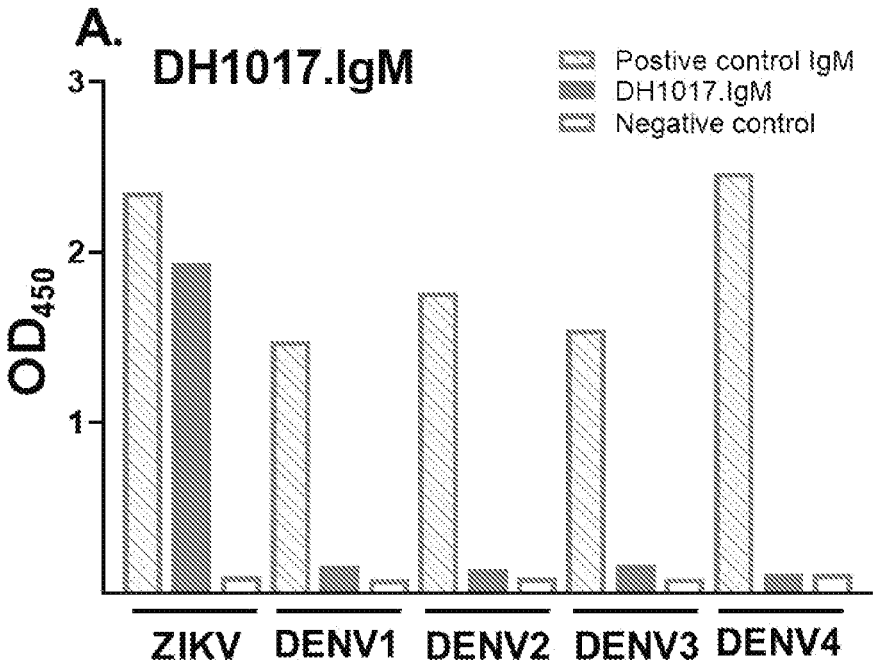

FIGS. 9A and B show DH1017.IgM and DH1017.IgG are specific to ZIKV and do not cross-react with DENV serotypes 1, 2, 3 and 4. Binding to ZIKV and DENV 1—was measured via virion capture ELISA. Positive control for each assay is shown in the hatched bars, and blank bars represent negative control. Sample is indicated in the solid bar. Magnitude of binding to Zika virus and Dengue virus serotypes 1-4 shown for DH1017.IgM (9A, solid bar). Antibody binding to the virus was assess via a virus-capture ELISA in a 96 well plate format. Antibody binding to the virus was measured at 100 ug/mL, and magnitude of binding was measured as optical density at 450 nm. We find that DH1017.IgM interacts specifically with Zika virus, and not with Dengue virus serotypes 1-4, like the DH1017.IgG recombinant monoclonal antibody produced with the same antigen-binding sites (9B). The positive controls are commercial mAbs that are known to interact with the corresponding virus, and negative controls indicate background level signal without any mAb present.

FIG. 10 (Attachment No. 1) shows annotated nucleotide and amino acid sequences of the immunoglobulin heavy chain (IgH) and light chain (IgL) variable region, V (D) J rearrangements. The table below shows the sequence identifiers for the sequences shown in FIG. 10.

| NUCLEOTIDE SEQUENCES | SEQ ID NO |
| --- | --- |
| Heavy Chain Sequences | |
| H621097 | 1 |
| H621157 | 2 |
| H621151 | 3 |
| H621162 | 4 |
| H621098 | 5 |
| H621099 | 6 |
| H621178 | 7 |
| H621180 | 8 |

6

-continued

| | |
| --- | --- |
| H621182 | 9 |
| H592679 | 10 |
| H621188 | 11 |
| Kappa Chain Sequences | |
| K620747 | 12 |
| K620780 | 13 |
| K620782 | 14 |
| K620748 | 15 |
| K620749 | 16 |
| K620790 | 17 |
| K620792 | 18 |
| K620793 | 19 |
| K620797 | 20 |
| Lambda Chain Sequences | |
| L620650 | 21 |
| L620584 | 22 |
| L620585 | 23 |
| L620663 | 24 |
| L590920 | 25 |

| AMINO ACID SEQUENCES | |
| --- | --- |
| Heavy Chain Sequences | |
| H621097 | 26 |
| H621157 | 27 |
| H621151 | 28 |
| H621162 | 29 |
| H621098 | 30 |
| H621099 | 31 |
| H621178 | 32 |
| H621180 | 33 |
| H621182 | 34 |
| H592679 | 35 |
| H621188 | 36 |
| Kappa Chain Sequences | |
| K620747 | 37 |
| K620780 | 38 |
| K620782 | 39 |
| K620748 | 40 |
| K620749 | 41 |
| K620790 | 42 |
| K620792 | 43 |
| K620793 | 44 |
| K620797 | 45 |
| Lambda Chain Sequences | |
| L620650 | 46 |
| L620584 | 47 |
| L620585 | 48 |
| L620663 | 49 |
| L590920 | 50 |

Figure 11A:
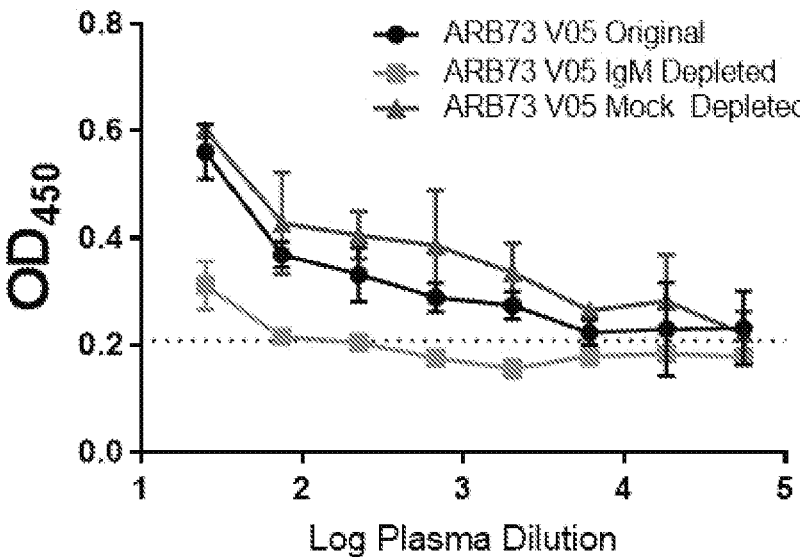
Figure 11B:
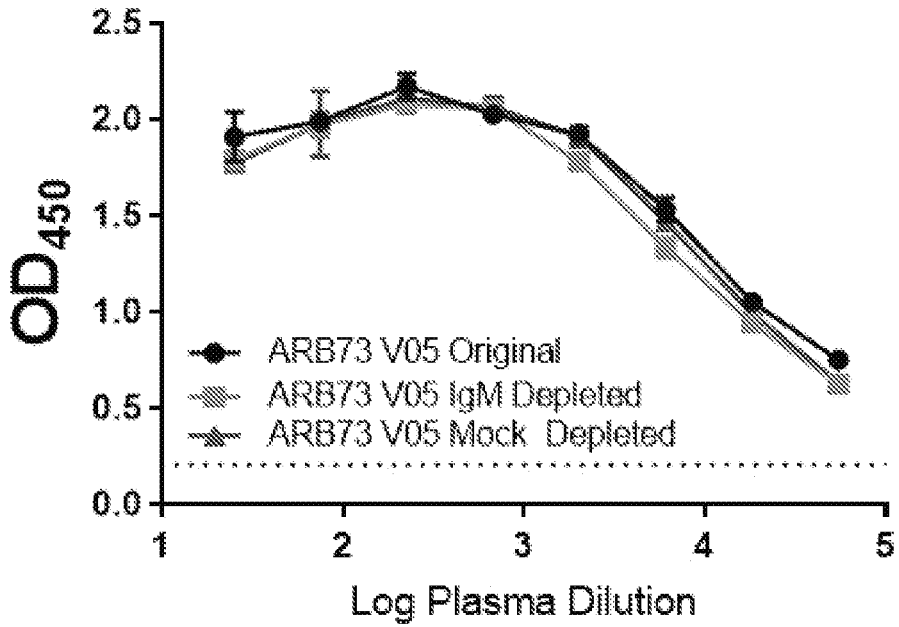
Figure 11C:
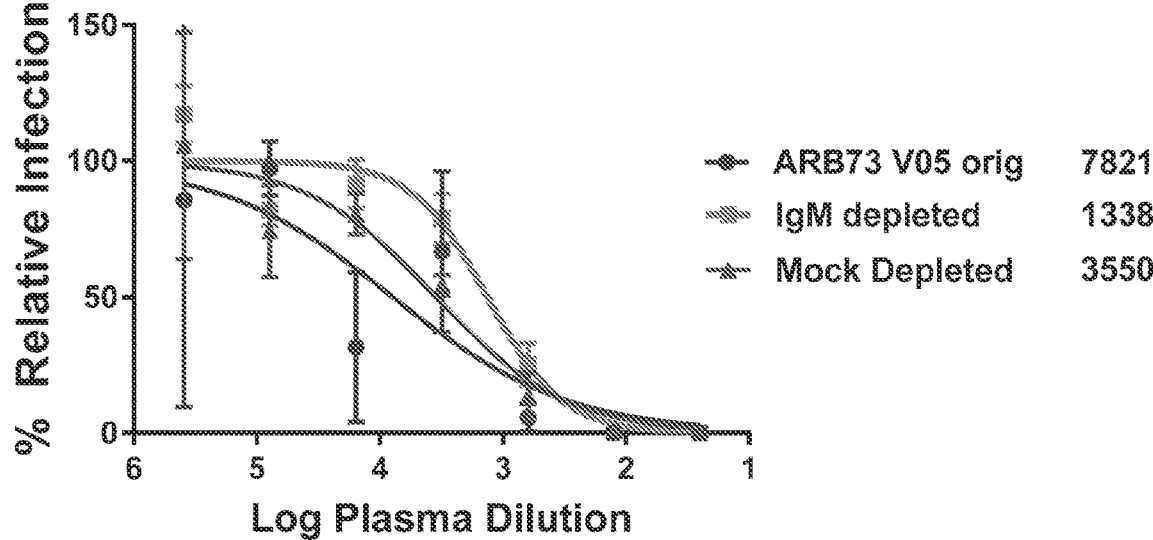

FIGS. 11A, 11B, and 11C show that IgM depleted plasma from the timepoint where DH1017.IgM was isolated shows reduced neutralization, indicating that IgM is involved in direct neutralization of ZIKV. Circles indicates original plasma, and squares indicates plasma where IgM was depleted. Mock depleted in triangles indicates plasma that went through a process similar to depletion but without the IgM-specific component, to account for non-specific losses to plasma antibodies. ZIKV-specific plasma binding antibodies were assessed by a virion-capture ELISA, with plasma diluted serially. The magnitude of binding was quantified by magnitude of optical density (OD) at 450 nm. ZIKV neutralization was measured by a Focus Reduction Neutralization Test (FRNT), where foci of infection can be visualized on a 96-well plate and enumerated for serial dilutions of plasma. Percent relative infection is the proportion of foci in the presence of plasma as compared to a virus-only well at each dilution. A) Magnitude of ZIKV-specific IgM show that IgM specifically was depleted from plasma but mock depletion retained similar magnitude of ZIKV-specific IgM as original sample. B) Magnitude of ZIKV-specific IgG was measured across samples. We demonstrated that, as expected, plasma IgM depletion did not accidentally reduce overall plasma IgG binding to ZIKV, indicating that ZIKV-binding IgG in sample were still present after IgM depletion at levels comparable to the original, non-IgM-depleted plasma. C) ZIKV neutralization was measured across IgM-depleted and non-depleted samples. Neutralization titers at 50% of maximal infection are shown for each sample. The mock-depleted sample neutralized half as well, as compared to the original sample. Importantly, IgM depleted plasma was half as potent in ZIKV neutralization as mock depleted sample. These data indicate that IgM in plasma contributes to neutralization of ZIKV.

Figure 12A:
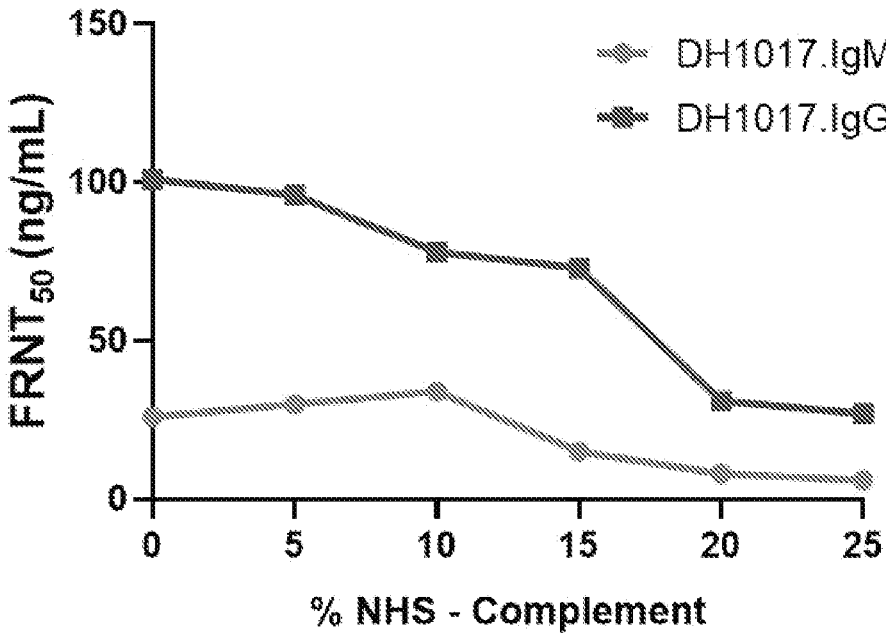
Figure 12B:
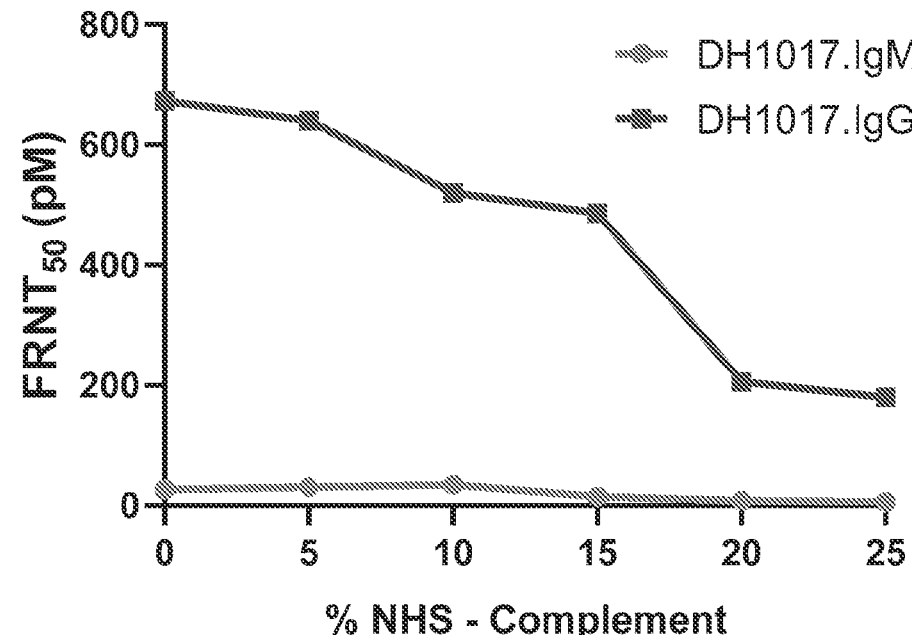

FIGS. 12A and 12B show that complement increases ZIKV neutralization potency of DH1017.IgM and DH1017.IgG monoclonal antibodies in a dose dependent manner. Neutralization potency is shown for DH1017.IgM and (circles) and DH1017.IgG (squares) with increasing concentrations of complement present. DH1017.IgM and DH1017.IgG share the same antigen binding sites but have different isotypes. Neutralization was assessed by FRNT in the presence of complement. The titer of 50% maximal ZIKV neutralizing activity (FRNT50) of each mAb was measured in the presence of complement. Complement from normal human serum (NHS) was tested at different proportions by total volume to examine a dose dependent effect. Neutralizing titer (FRNT50) of mAb with complement is relative to complement alone, indicating that the measured neutralizing titer is due to antibody-dependent complement activation. A) ZIKV neutralization titer is shown in nanograms per milliliter. B) ZIKV neutralization titer is shown in picomolar concentrations, accounting for the different sizes of IgM and IgG monoclonal antibodies. Data indicate that neutralization potency increases nearly 4-fold for both DH1017.IgM and DH1017.IgG in the presence of 25% complement as compared to no complement. Importantly, at each amount of complement present, DH1017.IgM neutralizes more potently than DH1017.IgG.

FIG. 13 shows the immunogenetics of Whole Zika virionbinding monoclonal antibodies. FIG. 13 is referred to as Table 1 throughout. The table below shows the sequence identifiers for the sequences shown in FIG. 13.

| | SEQ ID NO |
|---|---|
| CDR H3 SEQUENCE | |
| ARGRRGEWLVLHDAFDL | 51 |
| AKSWGDYYDSSGYPVYYYYYMDV | 52 |
| ARDIYYDSSGSRVRAAIDV | 53 |
| ARDLQDIILVAPNNFYHYYYMDV | 54 |
| TRRSEPLGDDAFDI | 55 |
| AKHNYYSNSWYAEDYYYYYMDV | 56 |
| ARHVGDLRVNDAFDI | 57 |
| ARDVGFKTTTDY | 58 |
| ASLSQSGGYQTYYFDY | 59 |
| ARDSSGWYYYHSSGYIKAFDY | 60 |
| VREGAKSGYDILTGYYDPYYYYGMDV | 61 |
| CDR L3 SEQUENCE | |
| QQYGSTPPYT | 62 |
| MQALQTPYT | 63 |
| QMWDVTRDQYV | 64 |
| QQYNNWPLT | 65 |
| QQYNNWPT | 66 |
| QVWDSNTDQYV | 67 |

-continued

| | SEQ ID NO |
|---|---|
| QQRTNWPLT | 68 |
| GTWDRSLSVVV | 69 |
| QQRSNWPPMYT | 70 |
| QVWDSSSDHEV | 71 |
| QQYGSSPPVFT | 72 |
| QQSYSTPPST | 73 |
| QQSYSSLWT | 74 |

DETAILED DESCRIPTION

The present invention relates to antibodies, and antigenbinding fragments thereof, that bind specifically to Zika virus (ZIKV) epitopes. Such antibodies potently neutralize infection of Zika virus (ZIKV) and can be used as therapeutic and diagnostic agents. The invention also relates to nucleic acids that encode the antibodies and antibody fragments and immortalized B cells that produce such antibodies and antibody fragments. In addition, the invention relates to the use of the antibodies and antibody fragments of the invention in screening methods as well as in the diagnosis, prevention and treatment of ZIKV infection.

Zika virus (ZIKV), a mosquito-borne Flavivirus, is a public health emergency. ZIKV was first isolated from macaques in 1947 in the Zika forest in Uganda (G. W. A. Dick, S. F. Kitchen, A. J. Haddow, Zika virus. I. Isolations and serological specificity. Trans. R. Soc. Trop. Med. Hyg. 46, 509-520 (1952)) and the first human infection was reported in Nigeria in 1954 F. N. Macnamara, Zika virus: a report on three cases of human infection during an epidemic of jaundice in Nigeria. Trans. R. Soc. Trop. Med. Hyg. 48, 139-145 (1954)).

Since then, ZIKV infections were sporadically reported in Africa and southeast Asia (D. Musso, Van Mai Cao-Lormeau, D. J. Gubler, Zika virus: following the path of dengue and chikungunya? The Lancet. 386, 243-244 (2015)), but epidemics were reported in Micronesia in 2007 (M. R. Duffy et al., Zika virus outbreak on Yap Island, Federated States of Micronesia. N Engl J Med. 360, 2536-2543 (2009)) and in French Polynesia in 2013-14, with the virus subsequently spreading to other countries in the Oceanian continent (V.-M. Cao-Lormeau, D. Musso, Emerging arboviruses in the Pacific. Lancet. 384, 1571-1572 (2014); D. Musso. E. J. Nilles, V.-M. Cao-Lormeau, Rapid spread of emerging Zika virus in the Pacific area. Clin. Microbiol. Infect. 20, O595-6 (2014)). After its introduction into Brazil in 2015, ZIKV has spread rapidly and in February 2016 the World Health Organization (WHO) declared it a Public Health Emergency of International Concern (L. R. Baden, L. R. Petersen, D. J. Jamieson, A. M. Powers, M. A. Honein, Zika Virus. N. Engl. J. Med. 374, 1552-1563 (2016); A. S. Fauci, D. M. Morens, Zika Virus in the Americas-Yet Another Arbovirus Threat. N Engl J Med, 160113142101009 (2016); D. L. Heymann et al., Zika virus and microcephaly: why is this situation a PHEIC? Lancet. 387, 719-721 (2016)). The main route of ZIKV infection is through bites by Aedes mosquitos, but the virus may also be sexually (D. Musso et al., Potential sexual transmission of Zika virus. Emerg Infect Dis. 21, 359-361 (2015)) and vertically transmitted (J. Mlakar et al., Zika Virus Associated with Microcephaly. N Engl J Med. 374, 951-958 (2016)). While most of the ZIKV infections are asymptomatic or cause only mild symptoms, there is evidence that ZIKV infection can lead to neurological complications, such as Guillain-Barre Syndrome in adults (V.-M. Cao-Lormeau et al., Guillain-Barre Syndrome outbreak associated with Zika virus infection in French Polynesia: a case-control study. Lancet. 0 (2016), doi:10.1016/S0140-6736(16)00562-6) and congenital birth defects including microcephaly in the developing fetus G. Calvet, R. S. Aguiar, A. Melo, S. A. Sampaio, Detection and sequencing of Zika virus from amniotic fluid of fetuses with microcephaly in Brazil: a case study. Lancet Infect Dis (2016), doi:10.1016/s1473-3099(16)00095-5; J. Mlakar et al., Zika Virus Associated with Microcephaly. N Engl J Med. 374, 951-958 (2016); E. J. Rubin, M. F. Greene, L. R. Baden, Zika Virus and Microcephaly. N Engl J Med (2016), doi:10.1056/NEJMe1601862), likely through its ability to infect human neural progenitor cells (H. Tang et al., Zika Virus Infects Human Cortical Neural Progenitors and Attenuates Their Growth. Stem Cell, 1-5 (2016)).

ZIKV belongs to the genus Flavivirus, which also includes the West Nile virus, dengue virus, tick-borne encephalitis virus, yellow fever virus, and several other viruses which may cause encephalitis. Flaviviruses are enveloped, with icosahedral and spherical geometries. The diameter is around 50 nm. Genomes are linear positive-sense RNA and non-segmented, around 10-11 kb in length. The genome of flaviviruses encodes 3 structural proteins (Capsid, prM, and Envelope) and 8 non-structural proteins (NS1, NS2A, NS2B, NS3, NS4A, NS4B, NS5 and NS5B).

While Flavivirus envelope (E) proteins mediate fusion and are the main target of neutralizing antibodies, the non-structural protein 1 (NS1) is secreted by infected cells and is involved in immune evasion and pathogenesis (D. A. Muller, P. R. Young, The Flavivirus NS1 protein: molecular and structural biology, immunology, role in pathogenesis and application as a diagnostic biomarker. Antiviral Res. 98, 192-208 (2013)). Two recent structural studies showed a high level of structural similarity between the E protein of ZIKV and that of other flaviviruses, such as dengue virus (DENV), yellow fever virus (YFV) and West Nile virus (WNV) but also revealed unique features that may be related to the ZIKV neurotropism (L. Dai et al., Structures of the Zika Virus Envelope Protein and Its Complex with a Flavivirus Broadly Protective Antibody. Cell Host Microbe (2016), doi:10.1016/j.chom.2016.04.013; D. Sirohi et al., The 3.8 Å resolution cryo-EM structure of Zika virus. Science, aaf5316 (2016)). Similarly, the structural analysis of ZIKV NS1 revealed conserved features with NS1 of other flaviviruses although with different electrostatic characteristics (J. Kim et al., Zika virus NS1 structure reveals diversity of electrostatic surfaces among flaviviruses, 1-6 (2016)).

A phenomenon that is characteristic of certain flaviviruses is the disease-enhancing activity of cross-reactive antibodies elicited by previous infection by heterologous viruses. In the case of Dengue virus (DENV), for which 4 serotypes are known, there is epidemiological evidence that a primary infection protects from reinfection with the same serotype, but represents a risk factor for the development of severe disease upon reinfection with a different serotype (S. B. Halstead, Dengue Antibody-Dependent Enhancement: Knowns and Unknowns. Microbiol Spectr. 2, 249-271 (2014)).

The exacerbated disease is triggered by E and prM-specific antibodies that fail to neutralize the incoming virus but instead enhance its capture by Fc receptor-expressing (FcR.sup.+) cells, leading to enhanced viral replication and activation of cross-reactive memory T cells. The resulting cytokine storm is thought to be the basis of the most severe form of disease known as dengue hemorrhagic fever/dengue shock syndrome (S. B. Halstead, Neutralization and anti-body-dependent enhancement of dengue viruses. Adv Virus Res. 60, 421-467 (2003); G. Screaton, J. Mongkolsapaya, S. Yacoub, C. Roberts, New insights into the immunopathology and control of dengue virus infection. Nat Rev Immunol. 15, 745-759 (2015)). The role of antibodies in severe dengue is supported by studies showing that waning levels of maternal antibodies in infants represent a higher risk for development of severe dengue disease (S. B. Halstead, Neutralization and antibody-dependent enhancement of dengue viruses. Adv Virus Res. 60, 421-467 (2003); S. B. Halstead et al., Dengue hemorrhagic fever in infants: research opportunities ignored. Emerging Infect Dis. 8, 1474-1479 (2002); T. H. Nguyen et al., Dengue hemorrhagic fever in infants: a study of clinical and cytokine profiles. J Infect Dis. 189, 221-232 (2004); A. L. Rothman, Dengue: defining protective versus pathologic immunity. J Clin Invest. 113, 946-951 (2004)).

Recently, it was shown that most antibodies that reacted to DENV envelope protein also bound to ZIKV, but those that recognize the major linear fusion-loop epitope (FLE) did not neutralize ZIKV and instead promoted antibody-dependent enhancement (ADE) of ZIKV infection (Dejni-rattisai W, Supasa P, Wongwiwat W, Rouvinski A, Barba-Spaeth G, Duangchinda T. Sakuntabhai A, Cao-Lormeau V M, Malasit P. Rey F A. Mongkolsapaya J, Screaton G R: Dengue virus sero-cross-reactivity drives antibody-dependent enhancement of infection with zika virus. Nat Immunol. 2016 Jun. 23. doi: 10.1038/ni.3515. PMID 27339099 [Epub ahead of print]).

Moreover, according to the WHO, the recent increase in cases of microcephaly and other neurological disorders potentially associated with Zika virus infection has prompted an increase in demand for laboratory testing to detect Zika virus infection. In this context, high specificity of the antibodies is required in order to distinguish ZIKV infection from infection of other flaviviruses. However, known anti-Zika antibodies are typically cross-reactive for other flaviviruses and, thus, not useful to distinguish ZIKV infection from infection of other flaviviruses.

In certain aspects the invention provides novel antibodies and fragments thereof, which specifically bind to ZIKV epitopes. In certain aspects, the invention provides potently neutralizing anti-ZIKV antibodies and fragments thereof. Such antibodies and fragments thereof do preferably not contribute to antibody-dependent enhancement (ADE) of Zika virus infection. It is also an object of the present invention to provide highly specific anti-ZIKV antibodies and fragments thereof useful in diagnosis and testing of ZIKV infection and diagnosis methods using such antibodies.

Antibodies Neutralizing Zika Virus

The present invention is based, amongst other findings, on the discovery and isolation of antibodies that bind specifically to Zika virus. The antibodies according to the present invention are expected to be highly effective in preventing as well as treating or attenuating Zika virus infection. Moreover, due to the specificity of the antibodies for Zika virus, it is expected that they do not elicit ADE, but rather block ADE. In diagnosis, Zika-specific antibodies provide an important tool for distinguishing Zika virus infection from infection with other flaviviruses, such as Dengue virus.

In a first aspect, the present invention provides an isolated antibody, or an antigen-binding fragment thereof, that specifically binds to a Zika virus epitope and neutralizes Zika virus infection. In non-limiting embodiments, the antibody, or the antigen-binding fragment thereof, according to the present invention, reduces viral infectivity of Zika virus.

Various neutralization assays are known in the art. For a neutralization assay, animal viruses are typically propagated in cells and/or cell lines. In non-limiting embodiments, the antibody and antigen binding fragment of the invention have high neutralizing potency.

Binding of an antibody may be assessed by use of a standard ELISA (enzyme-linked immunosorbent assay), which is well known to the skilled person.

In certain embodiments, the antibody, or an antigen-binding fragment thereof, according to the present invention does essentially not bind to Dengue virus-like particles and/or to Dengue envelope protein. In certain aspects, the antibody, or an antigen-binding fragment thereof, according to the present invention does essentially not bind to Dengue virus-like particles and/or to Dengue envelope protein of any of the four DENV serotypes DENV1, DENV2, DENV3 and DENV4.

In certain embodiments, the antibody, or an antigen-binding fragment thereof, according to the present invention does not contribute to antibody-dependent enhancement (ADE) of Zika virus infection. In certain embodiments, the antibody, or an antigen binding fragment thereof, according to the present invention blocks antibody-dependent enhancement (ADE) of Zika virus infection.

Production of Antibodies

Antibodies according to the invention can be made by any method known in the art. For example, the general methodology for making monoclonal antibodies using hybridoma technology is well known (Kohler, G. and Milstein, C. 1975; Kozbar et al. 1983).

In one embodiment, an alternative EBV immortalization method described in WO2004/076677 is used. In this method B cells producing the antibody of the invention are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

In another embodiments, EBV immortalization methods are described in WO2011/126577, WO2010/053987.

Another method is described in WO 2010/046775. In this method plasma cells are cultured in limited numbers, or as single plasma cells in microwell culture plates. Antibodies can be isolated from the plasma cell cultures. Further, from the plasma cell cultures, RNA can be extracted, and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

In some aspects, recombinant antibodies of the invention comprise antibodies purified from immortalized B cells. In some aspects, recombinant antibodies of the invention comprise antibodies produced by amplifying Ig genes and expressing these sequences in any suitable host cell.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, Nature Biotechnology 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T. PER.C6, NS0, myeloma or hybridoma cells. Mammalian cell lines suitable for expression of therapeutic antibodies are well known in the art.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. Alternatively, antibodies according to the invention may be produced by (i) expressing a nucleic acid sequence according to the invention in a host cell, e.g. by use of a vector according to the present invention, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain encoding mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Any suitable host cells could be used for transfection and production of the antibodies of the invention. The transfected host cell may be a eukaryotic cell, including yeast and animal cells, particularly mammalian cells (e.g., CHO cells, NS0 cells, human cells such as PER.C6 or HKB-11 cells, myeloma cells, or a human liver cell), as well as plant cells. In certain embodiments, expression hosts can glycosylate the antibody of the invention, particularly with carbohydrate structures that are not themselves immunogenic in humans. In one embodiment, the transfected host cell may be able to grow in serum-free media. In a further embodiment, the transfected host cell may be able to grow in culture without the presence of animal-derived products. The transfected host cell may also be cultured to give a cell line.

In certain aspects the invention provides nucleic acids encoding the inventive Zika antibodies. In non-limiting embodiments, the nucleic acids are mRNA, modified or unmodified, suitable for use any use, e.g. but not limited to use as pharmaceutical compositions. In certain embodiments, the nucleic acids are formulated in lipid, such as but not limited to LNPs.

In certain aspects, the invention provides nucleic acids comprising sequences encoding proteins of the invention. In certain embodiments, the nucleic acids are DNAs. In certain embodiments, the nucleic acids are mRNAs. In certain aspects, the invention provides expression vectors comprising the nucleic acids of the invention.

In certain aspects, the invention provides a pharmaceutical composition comprising mRNAs encoding the inventive antibodies. In certain embodiments, these are optionally formulated in lipid nanoparticles (LNPs). In certain embodiments, the mRNAs are modified. Modifications include without limitations modified ribonucleotides, poly-A tail, 5'cap.

In certain aspects the invention provides nucleic acids encoding the inventive protein designs. In non-limiting embodiments, the nucleic acids are mRNA, modified or unmodified, suitable for use any use, e.g. but not limited to use as pharmaceutical compositions. In certain embodiments, the nucleic acids are formulated in lipid, such as but not limited to LNPs.

Nucleic Acid Sequences

In some embodiments the antibodies are administered as nucleic acids, including but not limited to mRNAs which could be modified and/or unmodified. See US Pub 20180028645A1, US Pub 20090286852, US Pub 20130111615, US Pub 20130197068, US Pub 20130261172, US Pub 20150038558, US Pub 20160032316, US Pub 20170043037, US Pub 20170327842, U.S. Pat. Nos. 10,006,007, 9,371,511, 9,012, 219, US Pub 20180265848, US Pub 20170327842, US Pub 20180344838A1 at least at paragraphs [0260]-[0281], WO/2017/182524 for non-limiting embodiments of chemical modifications, wherein each content is incorporated by reference in its entirety.

mRNAs delivered in LNP formulations have advantages over non-LNPs formulations. See US Pub 20180028645A1, WO/2018/081638, WO/2016/176330, wherein each content is incorporated by reference in its entirety.

In certain embodiments the nucleic acid encoding a protein is operably linked to a promoter inserted an expression vector.

In certain aspects the invention provides an expression vector comprising any of the nucleic acid sequences of the invention, wherein the nucleic acid is operably linked to a promoter. In certain aspects the invention provides an expression vector comprising a nucleic acid sequence encoding any of the polypeptides of the invention, wherein the nucleic acid is operably linked to a promoter. In certain embodiments, the nucleic acids are codon optimized for expression in a mammalian cell, in vivo or in vitro. In certain aspects the invention provides nucleic acids comprising any one of the nucleic acid sequences of invention. In certain aspects the invention provides nucleic acids consisting essentially of any one of the nucleic acid sequences of invention. In certain aspects the invention provides nucleic acids consisting of any one of the nucleic acid sequences of invention. In certain embodiments the nucleic acid of the invention, is operably linked to a promoter and is inserted in an expression vector. In certain aspects the invention provides an immunogenic composition comprising the expression vector.

In certain aspects the invention provides a composition comprising at least one of the nucleic acid sequences of the invention. In certain aspects the invention provides a composition comprising any one of the nucleic acid sequences of invention. In certain aspects the invention provides a composition comprising at least one nucleic acid sequence encoding any one of the polypeptides of the invention. In certain aspects the compositions comprise a suitable carrier. In certain aspects the compositions comprise a suitable adjuvant.

In one embodiment, the nucleic acid is an RNA molecule. In one embodiment, the RNA molecule is transcribed from a DNA sequence described herein. In some embodiments, the RNA molecule is encoded by one of the inventive sequences. In another embodiment, the nucleotide sequence comprises an RNA sequence transcribed by a DNA sequence encoding the polypeptide sequence of the sequences described herein, or a variant thereof or a fragment thereof. Accordingly, in one embodiment, the invention provides an RNA molecule encoding one or more of inventive antibodies. The RNA may be plus-stranded. Accordingly, in some embodiments, the RNA molecule can be translated by cells without needing any intervening replication steps such as reverse transcription.

In some embodiments, a RNA molecule of the invention may have a 5' cap (e.g. but not limited to a 7-methylguanosine, 7mG(5')ppp(5')NlmpNp). This cap can enhance in vivo translation of the RNA. The 5' nucleotide of an RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. In some embodiments, a RNA molecule useful with the invention may be single-stranded. In some embodiments, a RNA molecule useful with the invention may comprise synthetic RNA.

The recombinant nucleic acid sequence can be an optimized nucleic acid sequence. Such optimization can increase or alter the immunogenicity of the protein. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

Methods for in vitro transfection of mRNA and detection of protein expression are known in the art.

Methods for expression and immunogenicity determination of nucleic acid encoded proteins are known in the art.

Pharmaceutical Composition

The present invention also provides a pharmaceutical composition comprising one or more of: (i) the antibody, or the antibody fragment thereof, according to the present invention; (ii) the nucleic acid encoding the antibody, or antibody fragments according to the present invention; (iii) the vector comprising the nucleic acid according to the present invention; and/or (iv) the cell expressing the antibody, or antibody fragments according to the present invention or comprising the vector according to the present invention.

In certain aspects, the invention provides a pharmaceutical composition comprising the antibody, or the antigen-binding fragment thereof, according to the present invention, the nucleic acid according to the present invention, the vector according to the present invention and/or the cell according to the present invention.

The pharmaceutical composition may also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. In certain embodiments the pharmaceutically acceptable carrier in a pharmaceutical composition according to the present invention is not an active component in respect to Zika virus infection.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody or antibody fragment may be provided in kit form with sterile water or a sterile buffer.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody or antibody fragment molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies or antibody fragments according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. In certain embodiments, the pharmaceutical composition may be prepared for oral administration, e.g. as tablets, capsules and the like, for topical administration, or as injectable, e.g. as liquid solutions or suspensions. In certain embodiments, the pharmaceutical composition is an injectable. Solid forms suitable for solution in, or suspension in, liquid vehicles prior to injection are also contemplated, e.g. that the pharmaceutical composition is in lyophilized form.

For injection, e.g. intravenous, cutaneous or subcutaneous injection, or injection at the site of affliction, the active ingredient could be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is in a "prophylactically effective amount" or a "therapeutically effective amount", this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and cornstarch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule. In particular, the pharmaceutical composition may be provided as single-dose product. In certain embodiments, the amount of the antibody or antibody fragment in the pharmaceutical composition—in particular if provided as single-dose product—does not exceed 200 mg. In certain embodiments, the amount does not exceed 100 mg, and in certain embodiments, the amount does not exceed 50 mg.

In non-limiting embodiments, the antibodies or antibody fragments of the invention could be used for non-therapeutic uses, such as but not limited to diagnostic assays.

Sequence Variants and Identity

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; www.ncbi.nlm.nih-.gov/) [Blosum 62 matrix; gap open penalty=11 and gap extension penalty=1].

The antibodies or antibody fragments of the invention and pharmaceutical compositions comprising these antibodies or antibody fragments, whether are recombinant proteins, purified IgM antibody, or nucleic acids encoding these, or vectors comprising nucleic acids encoding these, are contemplated for use in various therapeutic and/or prophylactic methods. In certain embodiments, the antibodies or antibody fragments are administered in a therapeutic amount to a subject in need thereof. The antibodies or antibody fragments could be administered pre- and post-exposure. The subject could be exposed to Zika. The subject could be pregnant or expecting to become pregnant.

EXAMPLES

Example 1

Isolation of ZIKV-Specific Monoclonal Antibodies from Pregnant Women Enrolled in a Prospective Cohort in Brazil

Background

Congenital transmission of Zika virus (ZIKV) in ~7-14% of infants born to ZIKV-infected pregnant women may lead to lifelong morbidity with symptoms like microcephaly, neurodevelopmental defects, visual impairment, and motor dysfunction [Rasmussen et al., 2016 N Engl J Med 2016; 374:1981-1987; Reynolds et al., 2017 MMWR Morb Mortal Wkly Rep 2017; 66:366-373]. As of now, there are no vaccines to prevent ZIKV infections. Thus, therapeutic and prophylactic interventions are urgently needed to prevent vertical transmission and mitigate the severity of the birth defects that are collectively named Congenital Zika Syndrome (CZS). In mice and non-human primate models, it has been shown that antibodies elicited by candidate vaccines or natural infection can protect against heterologous ZIKV challenge, clearly indicating the role of antibodies in mediating protection [Richner et al Cell 2017 Jul. 13; 170(2): 273-283.e12; Sapparapu et al. Nature 2016 Dec. 15; 540 (7633):443-447 PMIDs: 28708997, 27819683, 28978754]. Yet, without on-going transmission of ZIKV in the population, clinical trials cannot effectively test candidate vaccines and bring these products to the market. As immunity from the recent epidemic wanes ZIKV will likely re-emerge in seasonal episodic outbreaks like dengue virus (DENV), and continue to be a cause of congenital infections without preventative options.

In the absence of licensed vaccines, passive administration of immunoglobulin to women who become infected during pregnancy may be a valuable prophylactic option and enable reduction in the neonatal burden of CZS during an outbreak. Immunoglobulin therapies have been safely and successfully used in pregnancy to treat maternal infection with varicella zoster virus as well as reducing the impact of maternal conditions such as Rh incompatibility. See e.g. Levin M J, Duchon J M, Swamy G K, Gershon A A (2019) Varicellazoster immunoglobulin (VARIZIG) administration up to 10 days after varicella exposure in pregnant women, immunocompromised participants, and infants: Varicella outcomes and safety results from a large, open-label, expanded-access program. PLoS ONE 14(7):e0217749 [PMIDs: 6326634, 29624682, 21262937]. These interventions improve infant outcomes and could be leveraged to prevent CZS, reduce vertical transmission, or reduce severity of fetal disease. To identify potential prophylactic antibodies from ZIKV-infected pregnant Brazilian women whose infant was not affected by CZS, we isolated memory B cells that reacted with the whole Zika virion and produced soluble monoclonal antibodies in vitro that react with ZIKV and may be suitable for therapeutic and preventative interventions. Moreover, we tested for DENV cross-reactivity as the ideal monoclonal antibody for intervention would one that does not cross react with other flaviviruses due to concerns about antibody dependent enhancement of co-endemic flaviviruses. Thus, a ZIKV-specific mAb is an optimal candidate for antibody-based intervention.

Isolation of ZIKV-Specific Monoclonal Antibodies.

A mother-infant prospective cohort was established in the city of Vitória, which is the capital of the State of Espirito Santo in Brazil, and participants in this study were enrolled starting July 2016, at the time of the Zika epidemic. This prospective cohort study was approved by the Institutional Review Board of Hospital Cassiano Antonio Moraes, Brazilian National Research Ethics Committee (CEP/CONEP Registration number: 52841716.0.0000.5071), and Duke University Medical Center Institutional Review Board (Pro00100218). Sample collection and study design are described in Singh T et al. PLoS Negl Trop Dis 2019 Aug. 26; 13(8):e0007648, PMID 314,49521 epub ahead of print.

For monoclonal antibody (mAb) isolation we selected subjects based upon protective maternal immunity as defined by no microcephaly of the infant at birth, and high ZIKV binding and neutralization plasma antibody responses in pregnancy. We selected a time point for mAb isolation based on resolution of viremia, peak ZIKV neutralization titer, greater than 21 days post symptoms when memory B cells would likely be established, and PBMC sample availability. Because flavivirus antibody responses are highly cross-reactive in early convalescence but become more specific over time, we selected early and late convalescent time points for mAb isolation per subject [Collins et al. Emerg Infect Dis 2017 May; 23(5):773-781, PMID: 2841292].

One subject (ARB73) within our cohort defined an insightful case as she had prolonged viremia of nearly 40 days in pregnancy, whereas ZIKV is typically an illness of <10 days in healthy non-pregnant adults. Though prolonged viremia has been noted across multiple studies in pregnancy [Meaney-Delman et al., 2016 MMWR Morb Mortal Wkly Rep 2016; 65:211-214; Driggers et al., 2016 N Engl J Med 2016 Jun. 2; 374(22):2142-51; Suy et al., 2016], such cases are particularly challenging to detect and sample outside of prospective cohorts since the initial guideline was to only test for viremia within 2 weeks of infection. We reasoned that prolonged viremia could have led to further affinity maturation of ARB73's memory B cell responses as compared to other subjects with a shorter duration of viremia.

Therefore, to identify robust and matured ZIKV-specific antibody responses we studied memory B cells from ARB73. Moreover, this subject was previously exposed to DENV, which is co-endemic in this region, rendering high proportion of our cohort DENV seropositive. Therefore, we selected another subject with DENV pre-exposure but without prolonged viremia (ARB34).

Figure 1:
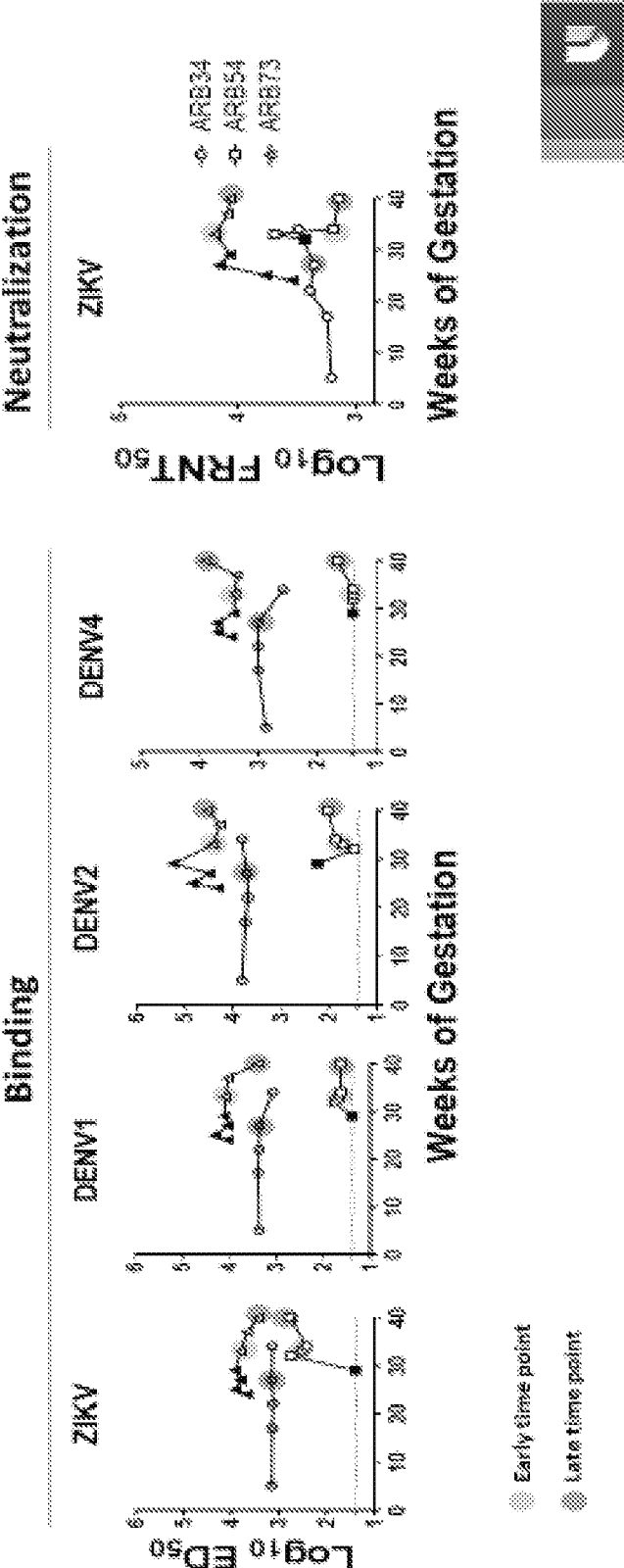
FIG. 1 shows flavivirus binding and neutralizing kinetics in maternal plasma throughout pregnancy. This indicates that peak ZIKV binding and neutralizing antibody responses are elicited within 1-2 weeks of ZIKV infection in pregnancy and sustained for the duration of gestation. Early and late time points in gestation that are selected for mAb isolation are indicated.
Figure 2A:
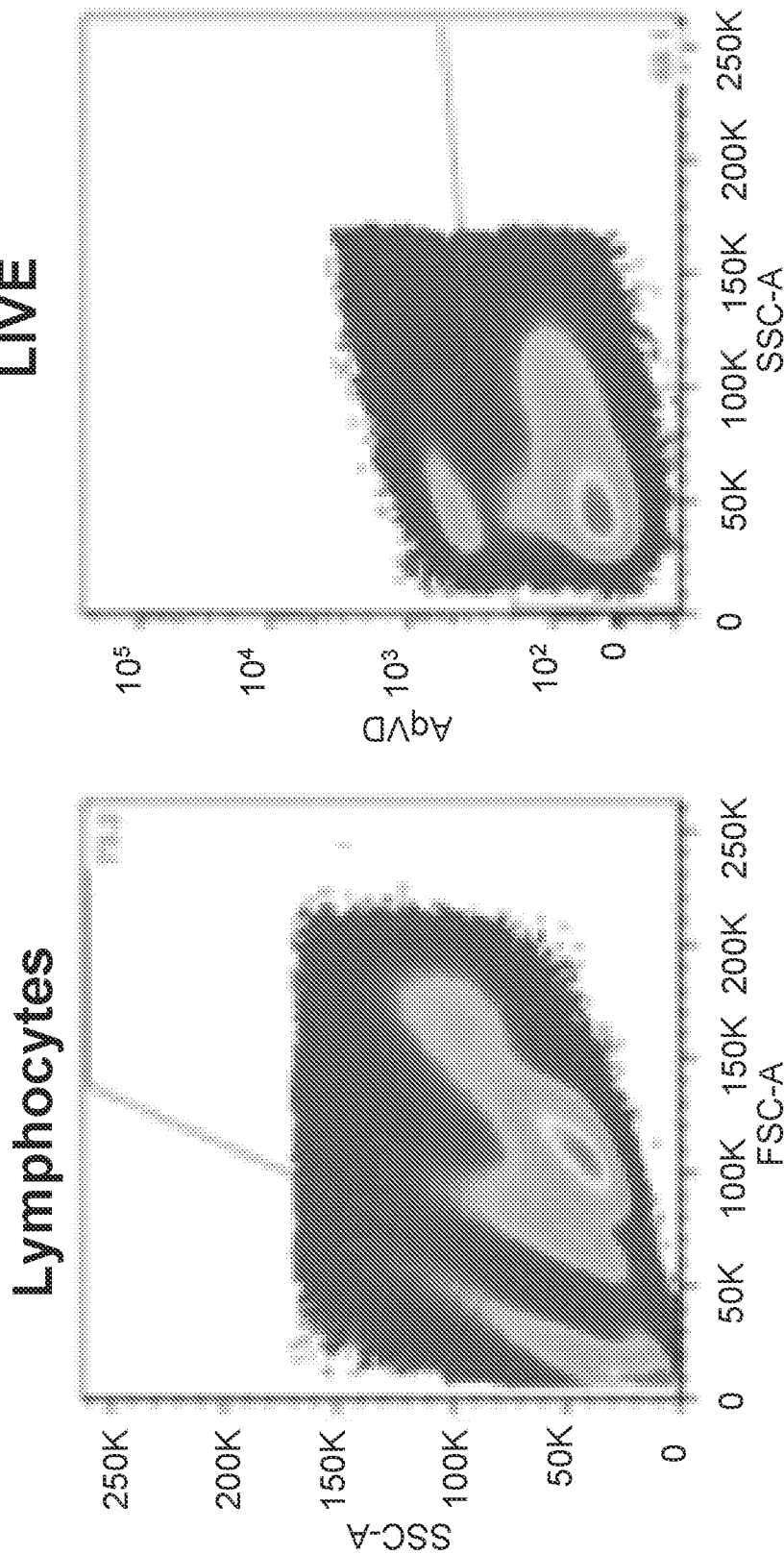
FIGS. 2A-B show gating strategy and sorting plots. The gating strategy to define ZIKV-binding B cells is shown for ARB73 (2A) and ARB34 (2B).
Figure 2A:
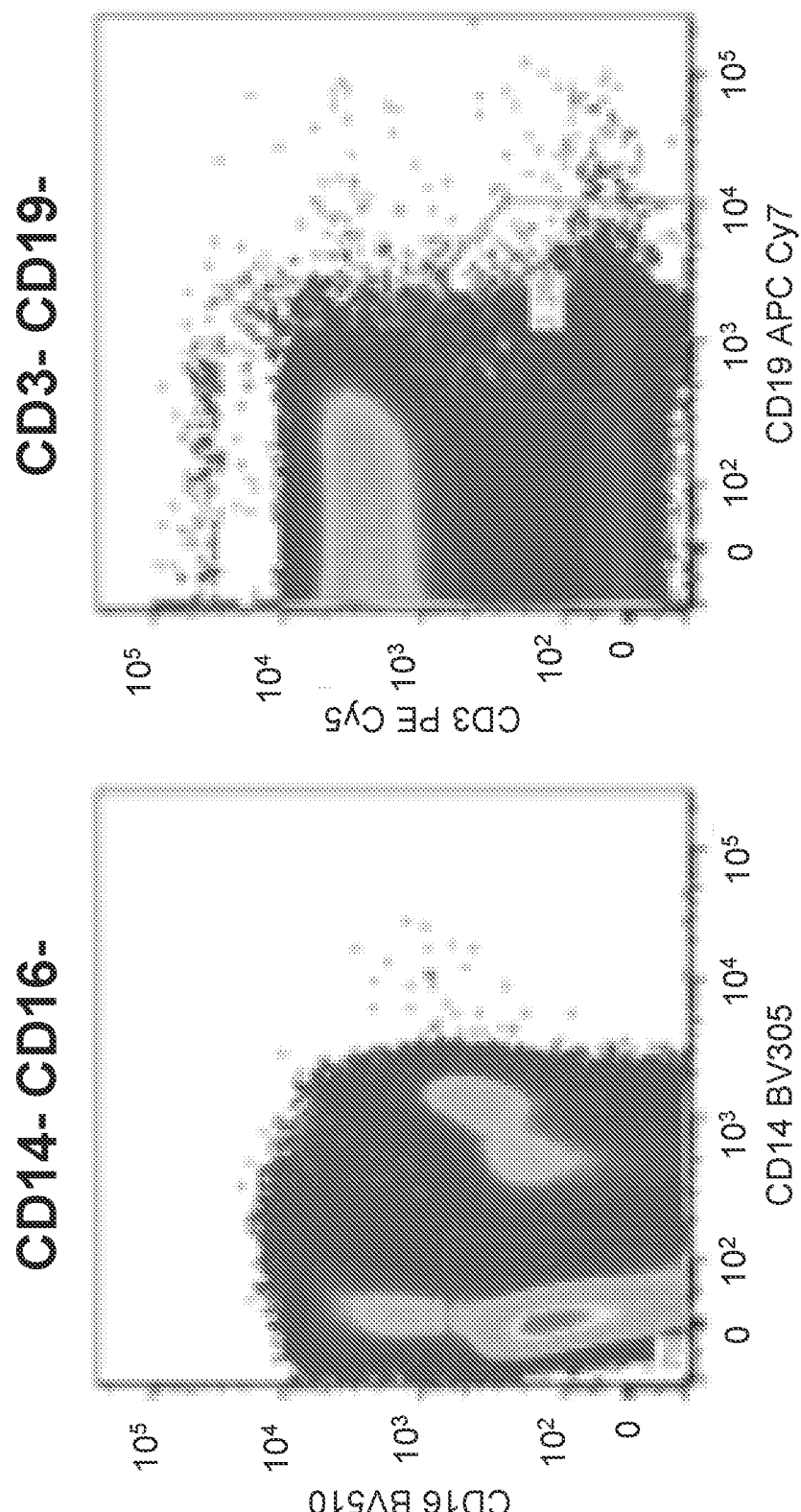
Figure 2A:
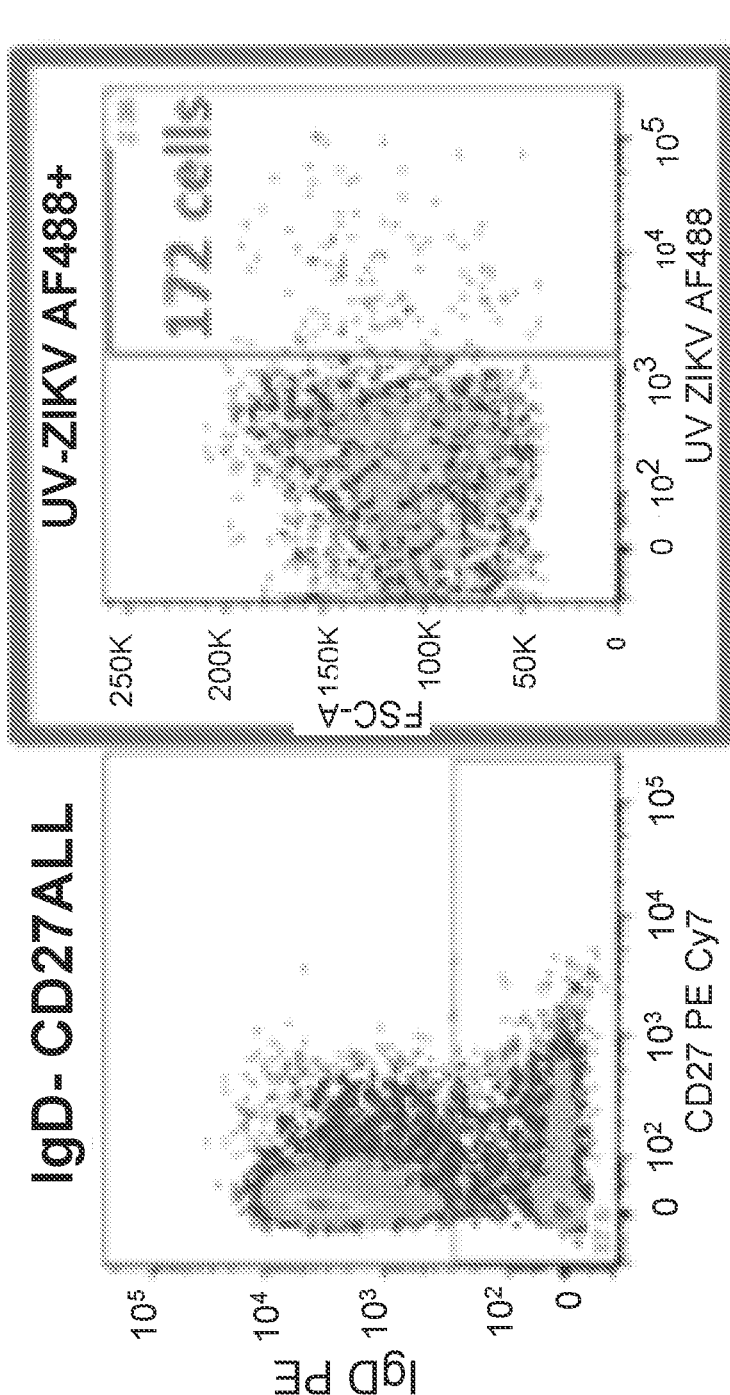
Figure 2B:
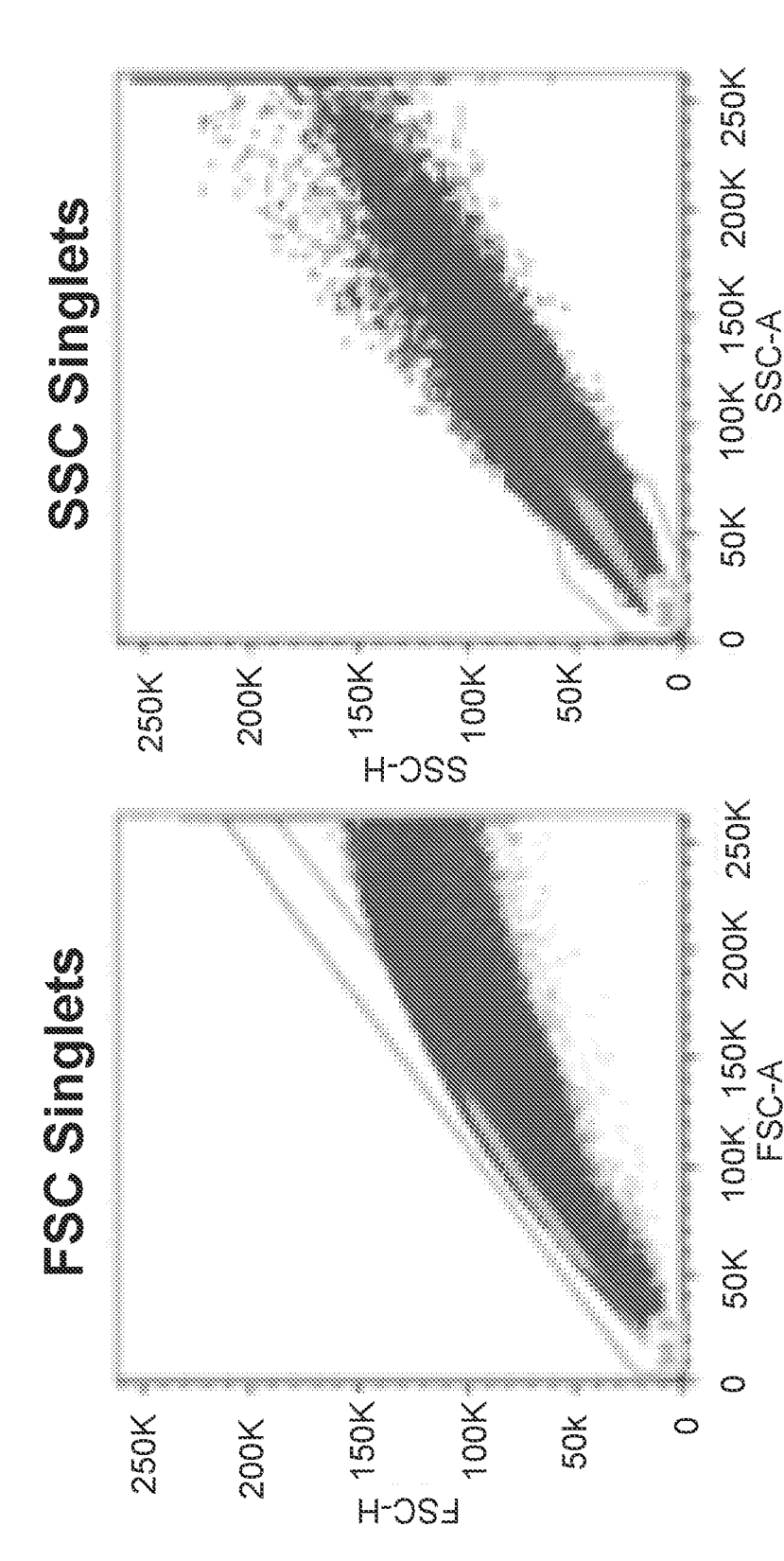
Figure 2B:
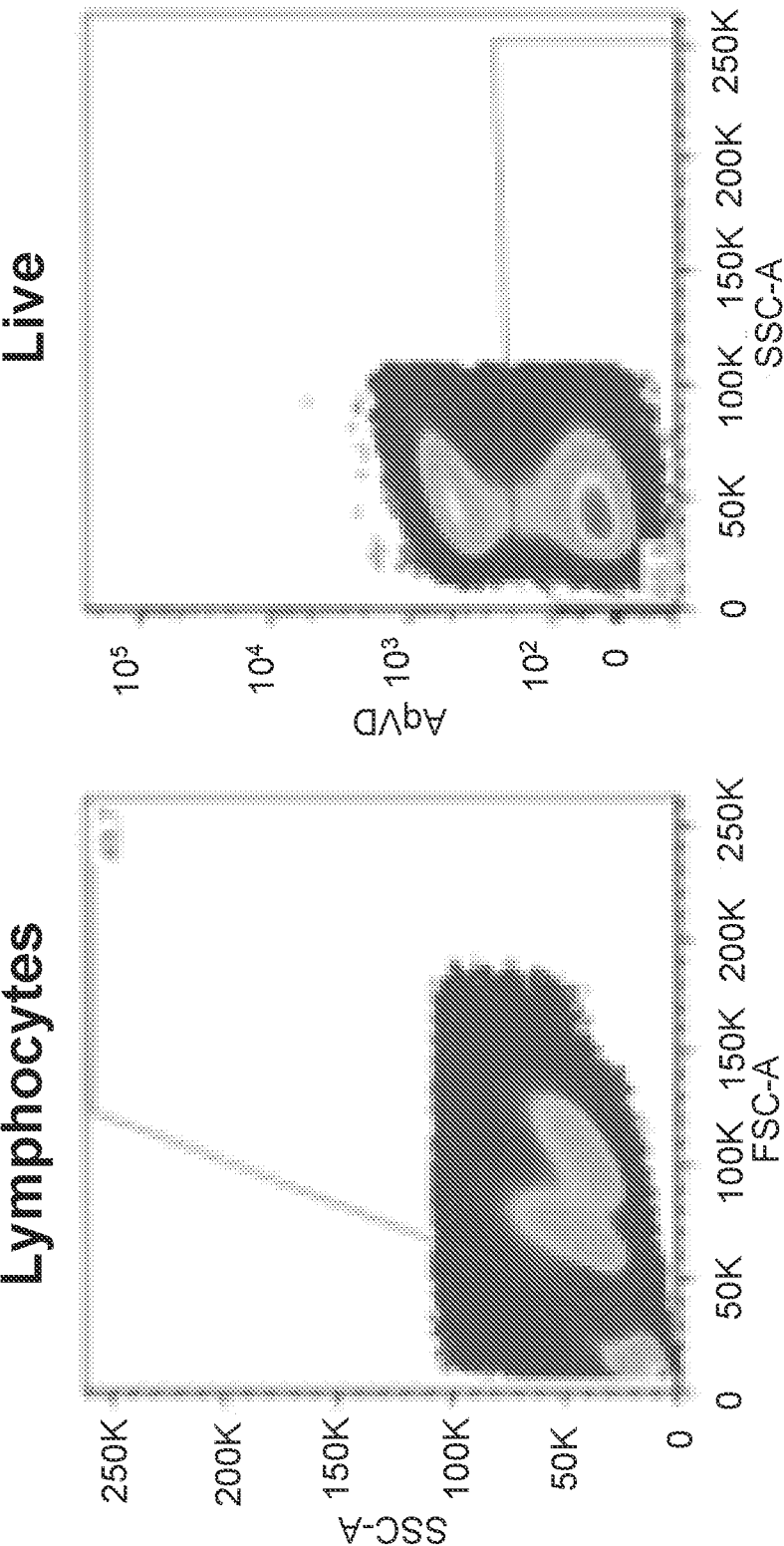
Figure 2B:
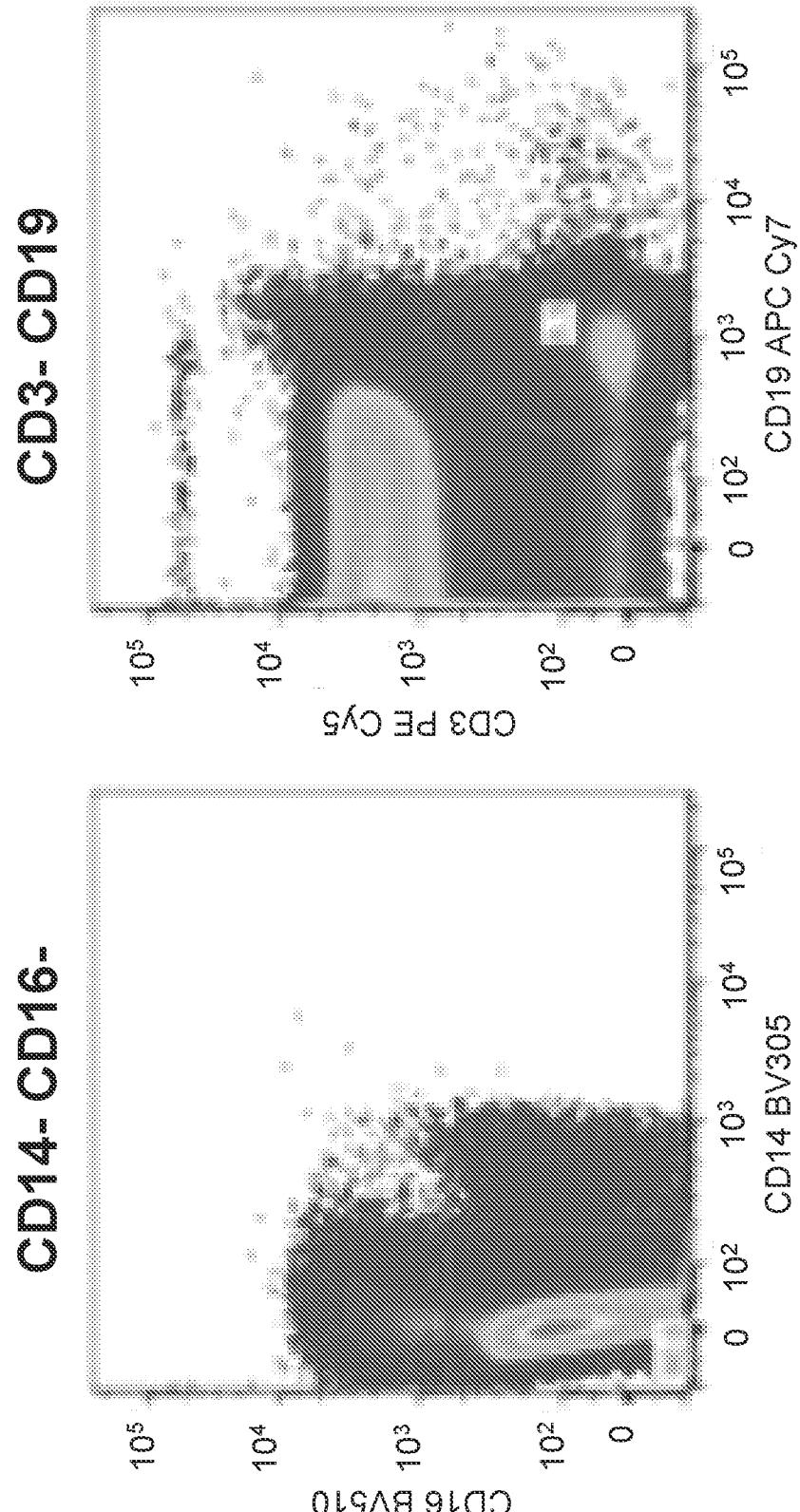
Figure 2B:
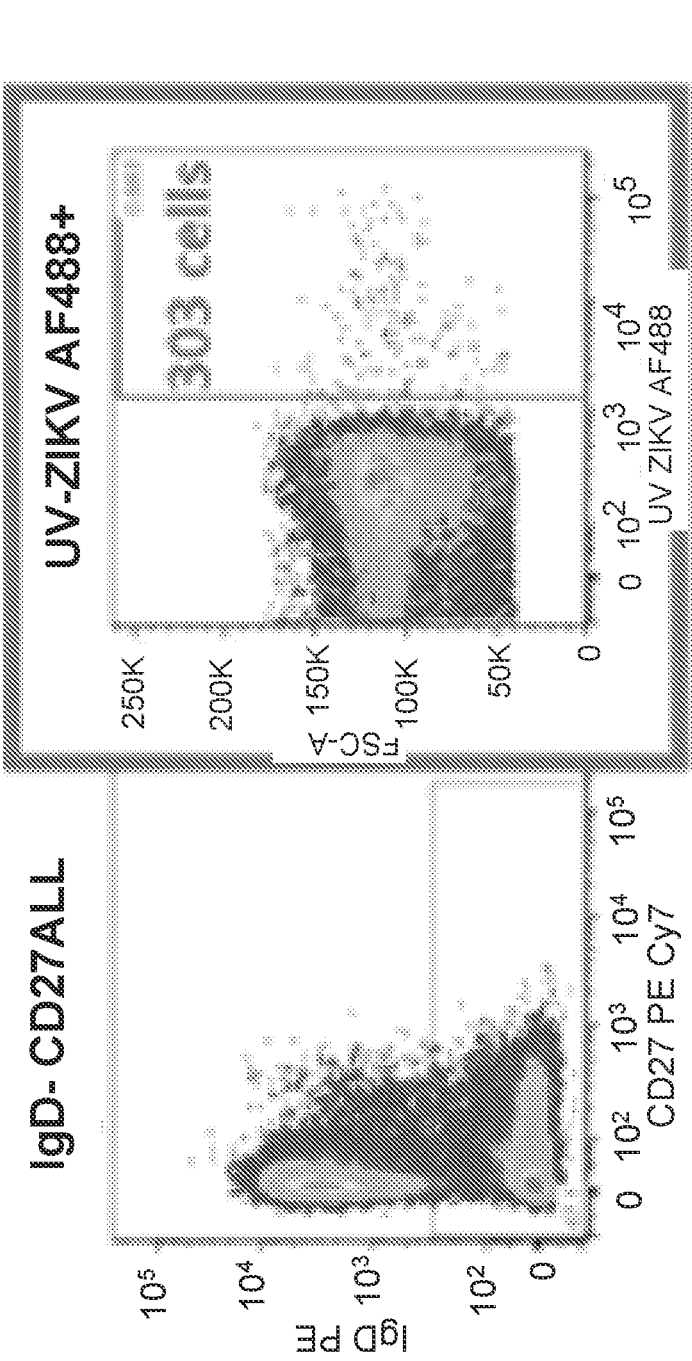

Herein we detail our progress on mAb isolation from PBMCs collected from two Brazilian pregnant women, ARB34 and ARB73, at 162 and 71 days post symptoms, respectively. Sample collection and storage methods are defined in Singh T et al. PLoS Negl Trop Dis 2019 Aug. 26; 13(8):e0007648, [PMID: 31449521]. Plasma antibody binding and neutralization responses assessed for the selection of these subjects for mAb isolation is shown in FIG. 1.

Memory B cells that reacted with fluorescently-labelled UV-inactivated ZIKV were flow sorted into B cell cultures. As shown in FIG. 2, from ARB34 and ARB73 pregnant women, we sorted a total of 303 and 172 Zika virus (ZIKV)-reactive memory B cells, respectively using a BD FACS Aria cell sorter. Memory B cells were defined by the following surface marker expression profile: $CD3^{neg}$, $CD14^{neg}$, $CD16^{neg}$, $CD19^{pos}$ and $IgD^{neg}$. ZIKV reactivity was defined by binding to AF488 fluorescently label on UV-inactivated ZIKV.

The flow-sorted memory B cells were cultured as described [Bonsignori et al. J Virol 2011 October; 85(19): 9998-10009, Bonsigori et al. Immunity 2018 Dec. 18; 49(6): 1162-1174.e8; PMIDs: 21795340, 30552024]. Briefly, cells were resuspended in cell culture medium containing Epstein Barr Virus (EBV) and incubated overnight. After infection with EBV, the cells were plated at a limited dilution in combination with CD40L-expressing feeder cells (we used MS40L cells [Luo et al. Blood 2009 Feb. 12; 113(7):1422-31; PMID: 19059876]), ODN2006, recombinant human IL-21 and CHK2-inhibitor to generate populations of clonally expanded immortalized B cells that differentiate into antibody-secreting cells in vitro [Bonsignori et al. J Virol 2011 October; 85(19):9998-10009; PMID: 21795340]. The cells were cultured for 14 days under these conditions to optimize the production of immunoglobulin [Bonsignori et al. J Virol 2011 October; 85(19):9998-10009; Bonsignori et al. Immunity 2018 Dec. 18; 49(6):1162-1174.e8; PMIDs: 21795340, 30552024]. After 14 days, the cell culture supernatants were tested for the presence of Ig. Supernatants from wells with detectable Ig at 14 days were used to identify the clonal populations that most effectively bound to ZIKV.

The stimulation regimen induces in vitro proliferation of individual memory B cell clones and differentiation into antibody-secreting cell lines. Some of these cell lines can become immortalized: in this case they will divide virtually indefinitely, and the cell line is called "stable".

The difference between a memory B cell and an antibody-secreting cells line is that memory B cells express B cell receptors (BCR) on the cell surface, which is constituted by plasma membrane-anchored Ig V(D)J rearrangements, but do not secrete antibodies. Whereas antibody-secreting cells secrete soluble immunoglobulins (i.e. antibodies) and do not express cell surface receptors. The antibody-secreting cell lines were derived after isolation and human manipulation of a memory B cell, which displays rearranged Ig VDJ sequences (VH and VL) as a B cell receptor (BCR) anchored on the surface. It is well known in the field that a memory B cell does not secrete antibodies. In vivo, a memory B cell may differentiate into plasma cells, which are capable of secreting antibody after activation and upon engagement with their cognate antigen. The VDJ sequences of the memory B cell receptor and the secreted antibody may or may not be the same, because antigen activation concurrently induces the process of somatic hypermutation, which introduces point mutations, insertions and/or deletions in the Ig V(D)J that alter the sequence and affinity of the secreted antibody.

Figure 3A:
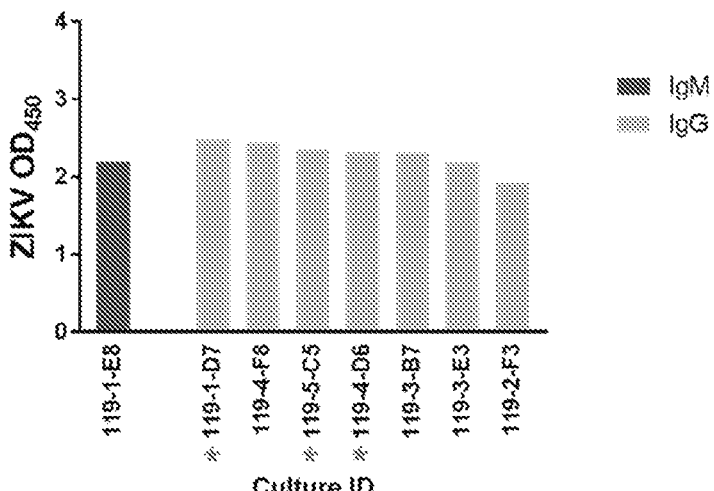
FIGS. 3A and 3B show ZIKV binding culture supernatants from ARB34 (3A top) and ARB73 (3B bottom). Binding was tested using secondary antibodies that differentiated IgM (blue) and IgG (orange) antibodies. Reactivity to whole virion ZIKV is expressed on the y-axis as optical density at the 450 nm wavelength (OD450). Asterisks indicate cultures from which we established stable cell lines
Figure 3B:
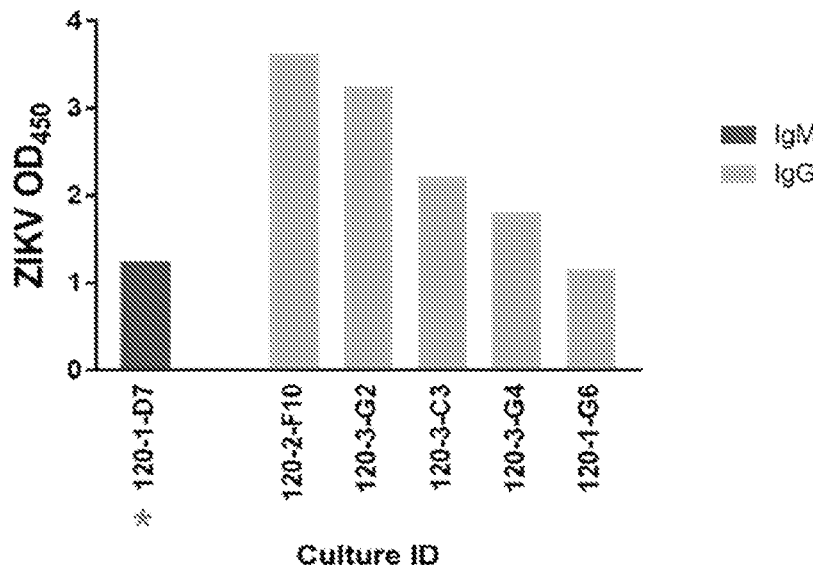

We used undiluted culture supernatants to test for ZIKV specificity in a whole virion capture ELISA. FIG. 3 summarizes the ZIKV binding results from this ELISA screening of the culture supernatants. From ARB34 (FIG. 3A, top), we confirmed 8 ZIKV-positive cultures. Of them, one was an IgM and 7 were IgG. From ARB73 (FIG. 3B, bottom), we obtained 6 ZIKV-positive cultures. Of them, 1 was an IgM and 5 were IgG. Four of these cell lines, marked with an asterisk in FIG. 3, were stable by virtue of EBV-mediated immortalization (in some figures cell lines are reported with an ".EBV" identifier). We sequenced the Ig V(D)J of the antibodies from either the stable, expanded cell lines or from the mRNA of cells collected after 14 days of culture for those that were not stable. In both cases we used the RT-PCR method and analyzed the immunoglobulin heavy chain (IgH) and light chain (IgL) variable regions (V(D)J), rearrangements as previously described [Liao et al. J Virol Methods 2009 June; 158(1-2):171-9; Gao et al. Cell 2014 Jul. 31; 158(3); PMIDs: 19428587, 25065977].

The immunogenetics of the sequences retrieved from each culture are shown in Table 1. The patient ID (PTID) from which each antibody was retrieved, the unique Ig heavy and light chain V(D)J identifiers (IgH ID and IgL ID, respectively) for each antibody, the Culture ID from which each antibody was retrieved, and the Antibody ID are listed in Table 2.

Annotated nucleotide and amino acid sequences of the immunoglobulin heavy chain (IgH) and light chain (IgL) variable region, V (D) J, rearrangements are listed in FIG. 10=Attachment 1. Each sequence includes the Ig V (D) J rearrangement. The complementarity-defining regions (CDR) heavy (H) and light (L) 1, 2 and 3 were defined using IMGT V-QUEST (www.imgt.org/IMGT_vquest/input) and are shown underlined and in bold. The order of CDRs is: for heavy chain, CDRH1, CDRH2 and CDRH3 and, for light chains, CDRL1, CDRL2 and CDRL3. For 119-3-B7, 119-4-F8, and 120-3-G2, we did not retrieve sequenceable amplicons. From culture 120-1-G4, we retrieved 2 heavy and 2 light chains, suggesting that two cells were sorted in the well. Of the heavy chains, one was of the IgG3 isotype and one was of the IgM isotype: as shown in FIG. 3, the ZIKV reactivity was detected for an IgG antibody. Therefore, the IgM sequence was not considered further. Future experiments will determine if both the light chain pairings with the IgG heavy chain retain ZIKV reactivity (Table 1 and Table 2). From cell line 119-4-D6, we retrieved 1 heavy chain and 3 light chains, as reported in Table 1 and Table 2; however, computational analysis indicates that the heavy chain is the IgM isotype, which is not what we observed experimentally to be the ZIKV-reactive isotype and may represent a sequence from a second cell accidentally sorted in the same well. The significance of two light chains retrieved from this culture sharing the same CDR L3 is unclear. Future experiments will determine if the recombinantly produced IgG monoclonal antibodies from 119-4-D6 use the pairings shown in Tables 1 and 2 and retain specificity, or if we can retrieve additional heavy chain sequences from this culture.

From the four stable cell lines, we affinity purified the monoclonal antibodies by gravity directly from the cell culture supernatants of EBV-transformed cells using Protein G and CaptureSelect IgM resins for IgG and IgM monoclonal antibodies, respectively. FIG. 4 shows the dose-dependent binding to ZIKV by all four purified monoclonal antibodies.

We next tested the ability of these 4 monoclonal antibodies to neutralize ZIKV. Neutralization assays were performed as described (Singh T et al. PLoS Negl Trop Dis 2019 Aug. 26; 13(8):e0007648, PMID: 31449521). As shown in FIG. 5, monoclonal antibodies 119-1-D7 and 119-5-C5 did not neutralize. Conversely, monoclonal antibody 119-4-D6 neutralized ZIKV with a $FRNT_{50}$ of 768 ng/ml and monoclonal antibody 120-1-D7 neutralized potently with $FRNT_{50}$=6.57 ng/ml. None of the antibodies neutralized DENV 1 through 4 ($FRNT_{50}$>5 ug/ml).

Since the 120-1-D7 IgM was purified directly from the cell line, it retained its polymeric form. FIG. 6 shows pictures of the 120-1-D7 IgM (which we have renamed DH1017.IgM) using negative stain electron microscopy. These data demonstrate that the purified DH1017.IgM monoclonal antibodies were present as pentamers. Some of the class averages in FIG. 6 also show the potential presence of a subpopulation of hexameric IgM. It is established that IgM can assume both pentameric and hexameric configurations, depending on the substitution of the J-chain with an additional Fab(2) monomer, which increases the number of Fabs on a single IgM from 10 to 12 (Hiramoto et al Sci. Adv. 2018; 4: eaau1199; Moh E S et al J Am Soc Mass Spectrom. 2016 July; 27(7):1143-55). Hexameric IgM is present in human serum at lower concentrations than pentameric IgM in healthy individuals (estimated at 5% of serum IgM in mice; Hughey C T et al. J. Immunol. 1998. 161, 4091-4097). Randall and colleagues demonstrated that hexameric IgM can be produced in vitro by upon stimulation by bacterial lipopolysaccharide (Randall T D et al. PNAS, 1992. 89: 962-966). Functionally, it has been reported that hexameric IgM may be a better complement activator than pentameric IgM (Hughey C T et al. J. Immunol. 1998. 161, 4091-4097; Davis, A C et al. Eur. J. Immunol. 1988: 18, 1001-1008; Collins C et al. Eur. J. Immunol. 2002: 32, 1802-1810). We demonstrated the ability of DH1017.IgM to mediate complement-dependent cell killing (FIG. 12).

Antibody isotype IgM data described in Ex1 used polymeric DH1017.IgM produced directly from the in vitro immortalized 120-1-D7 cell line. Methods for the recombinant production of polymeric IgM (both with and without J chain) have been described (Gilmour et al. Transfusion Medicine, 2008. 18:167-174).

Preliminary Epitope Mapping Indicates that DH1017.IgM Binds to a Conformational Epitope on the ZIKV E Protein.

To test if the DH1017 IgM monoclonal antibody was capable of binding and neutralizing as an IgG isotype mAb as well, we produced the same antibody recombinantly as an IgG1. We renamed 120-1-D7 as DH1017.IgM and named the recombinant IgG1 version DH1017.IgG. The recombinant DH1017.IgG was produced by cloning variable regions into expression cassettes as described by Gao, Bonsignori, Liao et al. Cell. 2014 Jul. 31; 158(3): 481-491 [PMID: 25065977].

FIG. 7 shows that DH1017.IgG retains binding to whole ZIKV with comparable similar $EC_{50}$ (46 ng/ml and 45 ng/ml for IgM and IgG, respectively). Since the molecular weight of IgM (~970 KDa) is higher than IgG (~150 KDa), there are fewer IgM molecules than IgG per amount or concentration in weight (i.e. ng/mL). Therefore, these $EC_{50}$ binding thresholds are equivalent to 474 pM and 3000 pM, respectively when comparing equal molar amounts. This ~6-fold difference is expected due to the polymeric nature of IgM as compared to the IgG and possibly reflects more than pentameric level of polymerization of the IgM on average.

FIG. 8 shows the neutralizing activity of DH1017.IgM and DH1017.IgG in a side-by-side experiment. The results confirmed the potent neutralization of DH1017.IgM ($FRNT_{50}$=24.7 ng/ml) and demonstrated that DH1017.IgG retains neutralizing activity ($FRNT_{50}$=149.5 ng/ml), indicating that neutralization is indeed a property of the V(D)J recombination. As for binding, we also calculated the $FRNT_{50}$ in moles, to account for the fact that a single IgM is significantly heavier (~970 KDa) than a single IgG (150 KDa). Expressed in picomolar (pM), the $FRNT_{50}$ DH1017.IgM is 25.5 pM and $FRNT_{50}$ of DH1017.IgG is 996.7 pM. Therefore, there is a ~40-fold difference in neutralizing activity when comparing equal numbers of molecules of the IgM and the IgG versions of the mAb. This is greater than 5-6-fold difference likely reflects the contribution of increased avidity with the IgM isotype as compared to the IgG isotype. Future experiments will determine the precise binding dynamics (affinity vs avidity).

Figure 9B:
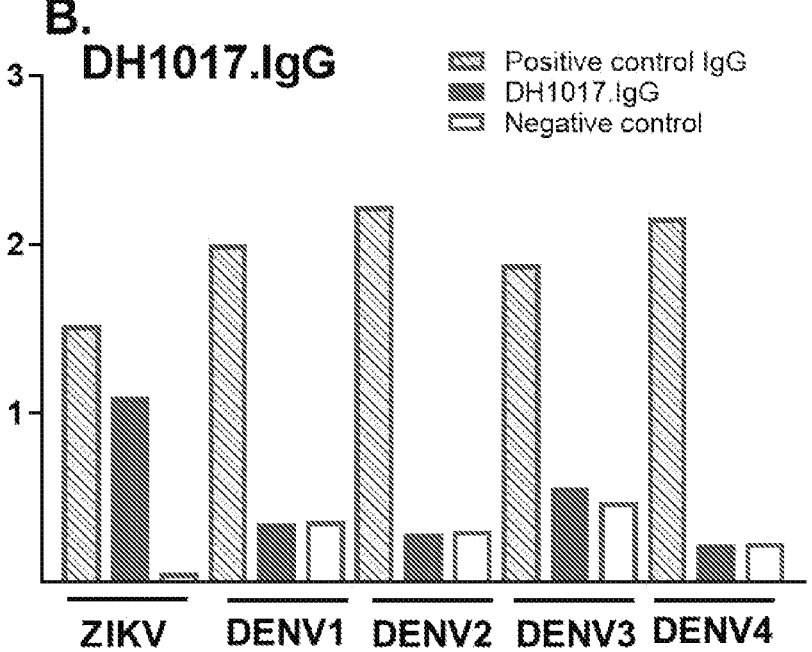

Finally, we assessed whether DH1017.IgM and DH1017.IgG were cross-reactive with dengue virus serotypes 1 through 4 in a virion binding ELISA, and found that this clone is specific to ZIKV and does not cross react with DENV (FIG. 9).

Table 1 showing the immunogenetics of Whole Zika virion-binding monoclonal antibodies is provided in FIG. 13.

The PTID is the de-identified ID for the subjects from which memory B cells were isolated. The IgH and IgL IDs uniquely identify each heavy and light chain V(D)J rearrangements isolated. Taken together, the IgH and IgL IDs univocally identify the IgH and IgL pairing of each monoclonal antibody, as shown in Table 1. The culture ID univocally identifies each culture well. Ab ID univocally identifies monoclonal antibodies, defined by a unique IgH and IgL pairing. Monoclonal antibodies from cultures in which only one heavy and one light chain were isolated were identified with the Culture ID. From culture wells in which multiple heavy and/or light chain sequences were isolated, monoclonal antibodies were identified using the Culture ID followed by a progressive number (e.g. "0.01", "0.02", etc.) to identify each unique IgH/IgL pairing. Antibody 120-1-D7 was subsequently renamed DH1017.IgM and the recombinant version expressed as IgG (which retains Ig V(D)J identical to that of DH1017.IgM) was named DH1017.IgG.

TABLE 2

| | Summary of the origin of the monoclonal antibodies. | | | |
|---|---|---|---|---|
| PTID | IgH ID | IgL ID | Culture ID | Ab ID |
| ARB34 | H621097 | K620747 | 119-1-D7 | 119-1-D7 |
| ARB34 | H621157 | K620780 | 119-1-E8 | 119-1-D8 |
| ARB34 | H621151 | L620650 | 119-2-F3 | 119-2-F3 |
| ARB34 | H621162 | K620782 | 119-3-E3 | 119-3-E3 |

TABLE 2-continued

| PTID | IgH ID | IgL ID | Culture ID | Ab ID |
|------|--------|--------|------------|-------|
| ARB34 | H621098 | K620748 | 119-4-D6 | 119-4-D6.01 |
| ARB34 | H621098 | L620584 | | 119-4-D6.02 |
| ARB34 | H621098 | L620585 | | 119-4-D6.03 |
| ARB34 | H621099 | K620749 | 119-5-C5 | 119-5-C5 |
| ARB73 | H621178 | K620790 | 120-3-C3 | 120-3-C3 |
| ARB73 | H621180 | K620792 | 120-1-G4 | 120-1-G4.01 |
| ARB73 | H621180 | L620663 | | 120-1-F4.02 |
| ARB73 | H621182 | K620793 | 120-1-G6 | 120-1-G6 |
| ARB73 | H592679 | L590920 | 120-1-D7 | 120-1-D7, also DH1017.IgM and DH1017.IgG |
| ARB73 | H621188 | K620797 | 120-2-F10 | 120-2-F10 |

Summary of the origin of the monoclonal antibodies.

Example 2

Antibodies of the invention will be further characterized in any suitable assay or animal model, to confirm their prophylactic or therapeutic use.

Future experiments include the expression of all the ZIKV-binding antibodies as recombinant proteins and the evaluation of multiple antiviral functions: direct virus neutralization, antibody-dependent cell cytotoxicity (ADCC), complement-dependent cytotoxicity (CDC) and antibody-dependent cellular phagocytosis (ADCP).

Therapeutic potential will also be evaluated in regard of the level of Fab multimerization and recombinant assembly with different Fc. As the data in Ex. 1 above indicate that a higher than dimeric multimerization (as in IgG) can have a strong impact on virus killing, we will evaluate the ability of higher levels of multimerization of virus killing in vitro and clearance in vivo. Also, IgM (by virtue of size and lack of IgG Fc) has a different bioavailability and distribution profile (e.g. Norderhaug I N et al. Crit Rev Immunol 1999. 19:481-508, Oyen et al. Nucl Med Commun 1996 17:616-20).

The therapeutic potential of ZIKV-specific mAbs will be evaluated through testing in animal models.

Antibodies of the invention could also be functionally compared to other Zika antibodies.

What is claimed is:

1. A recombinant Zika antibody or the antigen-binding fragment thereof, as selected from the group consisting of: 119-4-D6.01 having a VH consisting of H621098 with the amino acid sequence of SEQ ID NO: 30 and a VL consisting of K620748 with the amino acid sequence of SEQ ID NO: 40, 119-4-D6.02 having a VH consisting of H621098 with the amino acid sequence of SEQ ID NO: 30 and a VL consisting of L620584 with the amino acid sequence of SEQ ID NO: 47, 119-4-D6.03 having a VH consisting of H621098 with the amino acid sequence of SEQ ID NO: 30 and a VL consisting of L620585 with the amino acid sequence of SEQ ID NO: 48, DH1017.IgM having a VH consisting of H592679 with the amino acid sequence of SEQ ID NO: 35 and a VL consisting of L590920 with the amino acid sequence of SEQ ID NO: 50, and DH1017.IgG, having a VH consisting of H592679 with the amino acid sequence of SEQ ID NO: 35 and a VL consisting of L590920 with the amino acid sequence of SEQ ID NO: 50.

2. The antibody, or the antigen-binding fragment thereof, according to claim 1, wherein the antibody or antigen-binding fragment thereof, comprises a heavy chain comprising CDRH1, CDRH2 and CDRH3 and a light chain comprising CDRL1, CDRL2 and CDRL3, wherein the CDR comprises an amino acid sequence according to any of the CDR sequences in VH H592679 with the amino acid sequence of SEQ ID NO: 35 and a VL L590920 with the amino acid sequence of SEQ ID NO: 50.

3. The antibody, or the antigen-binding fragment thereof, according to claim 1, wherein the antibody is the antibody DH1017.IgM or DH1017.IgG.

4. The antibody, or the antigen-binding fragment thereof, according to claim 3, wherein the antibody, or the antigen-binding fragment thereof, is a purified antibody, a single chain antibody, Fab, Fab', F (ab) 2, Fv or scFv.

5. The antibody of claim 1, wherein the antibody is IgM or IgG isotype.

6. A pharmaceutical composition comprising the antibody, or the antigen-binding fragment thereof, of claim 1, and a pharmaceutically acceptable carrier.

7. A method for the treatment of Zika virus infection in a subject comprising administering to the subject a therapeutically effective amount of the pharmaceutical composition of claim 6.

8. A nucleic acid molecule comprising a polynucleotide encoding the antibody, or the antigen-binding fragment thereof, according to claim 1.

9. The nucleic acid of claim 8 wherein the nucleic acid is an mRNA, wherein the mRNA is suitable for use and delivery as a therapeutic mRNA.

10. A vector comprising the nucleic acid molecule according to claim 9.

11. A cell expressing the antibody, or the antigen-binding fragment thereof, comprising the vector according to claim 10.

12. A pharmaceutical composition comprising the vector according to claim 10.

13. The pharmaceutical composition according to claim 12 further comprising a pharmaceutically acceptable excipient, diluent or carrier.

14. A method of treating Zika infection in a subject in need thereof, comprising administering to the subject, the nucleic acid of claim 9 in an amount suitable to effect treatment of Zika infection.

15. The method of claim 14, wherein the subject is pregnant or expected to become pregnant.

* * * * *